United States Patent [19]

Weber et al.

[11] 3,932,503

[45] Jan. 13, 1976

[54] BENZENESULFONYL UREAS

[75] Inventors: Helmut Weber, Frankfurt am Main; Walter Aumüller; Karl Muth, both of Kelkheim, Taunus; Rudi Weyer, Frankfurt am Main, all of Germany

[73] Assignee: Hoechst Aktiengesellschaft, Frankfurt am Main, Germany

[22] Filed: May 25, 1970

[21] Appl. No.: 41,160

Related U.S. Application Data

[63] Continuation-in-part of Ser. No. 641,146, May 25, 1967, abandoned, and a continuation-in-part of Ser. No. 749,609, Aug. 2, 1968, abandoned, and a continuation-in-part of Ser. No. 10,659, Feb. 11, 1970, abandoned.

[52] U.S. Cl. ............... 260/553 DA; 260/332.2 A; 260/332.2 R; 424/275; 424/321
[51] Int. Cl.² ................................... C07C 127/16
[58] Field of Search ............ 260/553 DA, 332.2 A, 332.2 R

[56] References Cited
UNITED STATES PATENTS

| | | | |
|---|---|---|---|
| 3,426,067 | 2/1969 | Weber et al. | 260/553 DA |
| 3,454,635 | 7/1969 | Weber et al. | 260/553 DA |

FOREIGN PATENTS OR APPLICATIONS

| | | | |
|---|---|---|---|
| 654,561 | 4/1965 | Belgium | 260/553 DA |

*Primary Examiner*—Gerald A. Schwartz
*Attorney, Agent, or Firm*—Curtis, Morris & Safford

[57] ABSTRACT

Benzenesulfonyl-ureas having hypoglycemic activity and corresponding to the formula

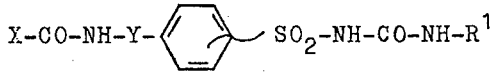

wherein $R^1$ is a. cyclopentyl, lower alkyl-cyclopentyl, dimethyl-cyclopentyl, tri-methyl-cyclopentyl, tetramethyl-cyclopentyl, chloro-cyclopentyl;

b. di-lower-alkyl-cyclohexyl, lower alkoxymethyl-cyclohexyl; chloro-cyclohexyl;

c. cycloalkenyl with 5-8 ring carbon atoms; methyl-cyclopentenyl, methyl-cyclohexenyl; di-methyl-cyclohexenyl, tri-methyl-cyclopentenyl;

X is

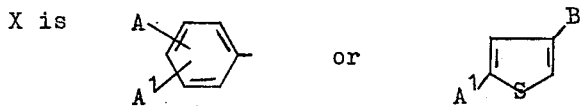

in which

A stands for hydrogen, halogen, lower alkyl, lower alkoxy, lower alkenoxy, methoxy-loweralkoxy, lower acyl, nitrophenyl or trifluoromethyl, $A^1$ stands for hydrogen, lower alkoxy, lower alkyl or halogen and B stands for hydrogen, lower alkyl, lower alkoxy, halogen, benzyloxy or methoxy-methoxy;

Y is a hydrocarbon chain of 1–3 carbon atoms, or a physiologically tolerable salt thereof.

9 Claims, No Drawings

BENZENESULFONYL UREAS

This application is a continuation-in-part of Application Ser. No. 641,146 filed May 25, 1967, Ser. No. 749,609 filed Aug. 2, 1968 and Ser. No. 10,659 filed Feb. 11, 1970 all of which are now abandoned.

The present invention relates to benzenesulfonylureas corresponding to the formula

which as such or in the form of their physiologically tolerable salts particularly their alkali or alkaline earth metal salts show hypoglycemic properties and are characterized by a strong and long lasting hypoglycemic action. In the formula:

$R^1$ is a. cyclopentyl, lower alkyl-cyclopentyl, di-methyl-cyclopentyl, tri-methyl-cyclopentyl; tetramethyl-cyclopentyl, chloro-cyclopentyl;

b. di-lower-alkyl-cyclohexyl, lower alkoxymethyl-cyclohexyl; chloro-cyclohexyl;

c. cycloalkenyl with 5-8 ring carbon atoms; methyl-cyclopentenyl, methyl-cyclohexenyl di-methyl-cyclohexenyl, tri-methyl-cyclopentenyl;

X is

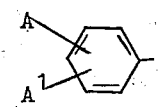 or 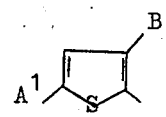

in which

A stands for hydrogen, halogen, lower alkyl, lower alkoxy, lower alkenoxy, methoxy-loweralkoxy, lower acyl, nitrophenyl or trifluoromethyl;

$A^1$ stands for hydrogen, lower alkoxy, lower alkyl or halogen and B stands for hydrogen, lower alkyl, lower alkoxy, halogen, benzyloxy or methoxy-methoxy;

Y is a hydrocarbon chain of 1-3 carbon atoms. According to the above-mentioned definitions, halogen may represent fluorine, chlorine, bromine or iodine; chlorine and bromine being preferred; lower alkyl or lower alkoxy may represent methyl, ethyl, propyl, isopropyl, n-butyl, tert.butyl or methoxy, ethoxy, propoxy, isopropoxy, tert.-butoxy, methyl or methoxy being preferred.

Ring systems representing the member X in the above mentioned formula are, for example, the following:

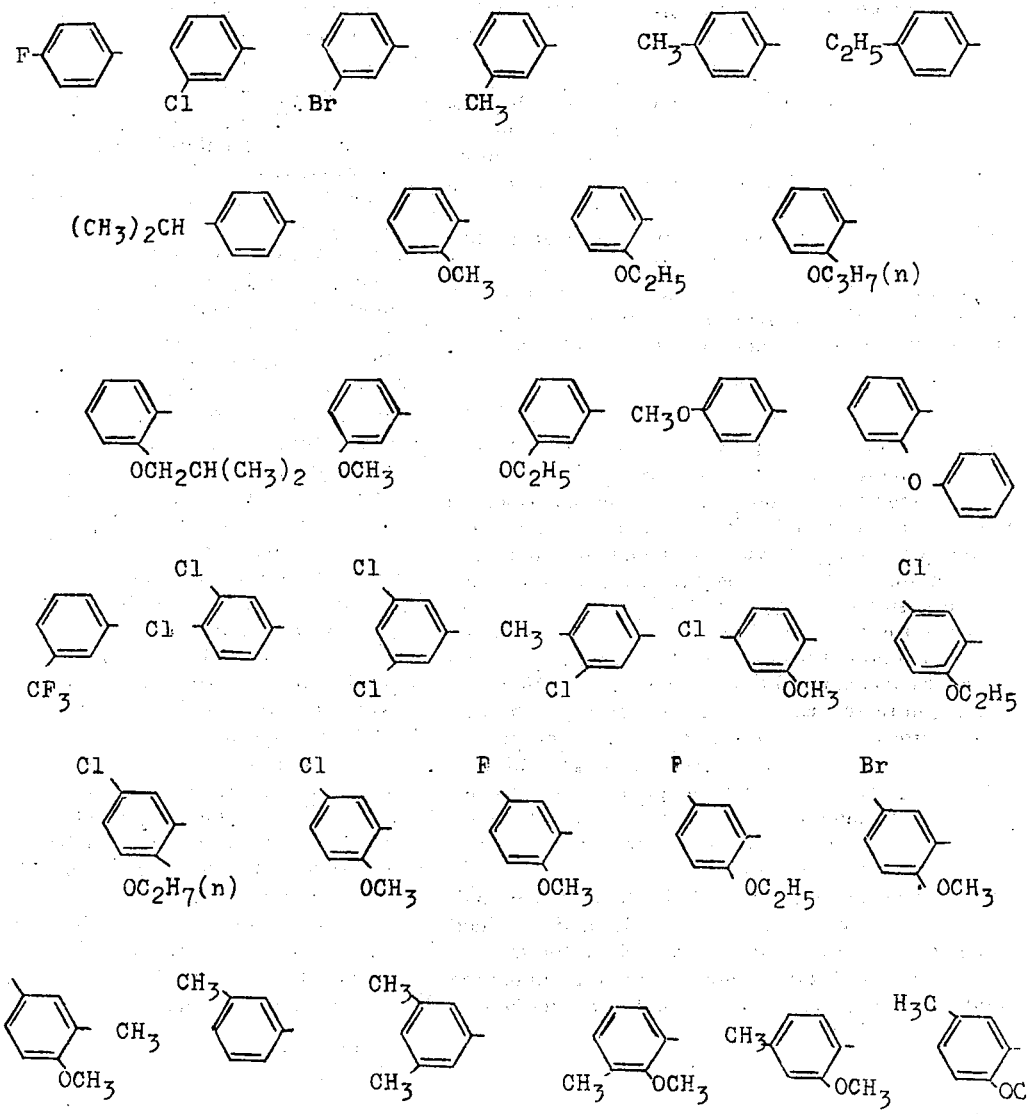

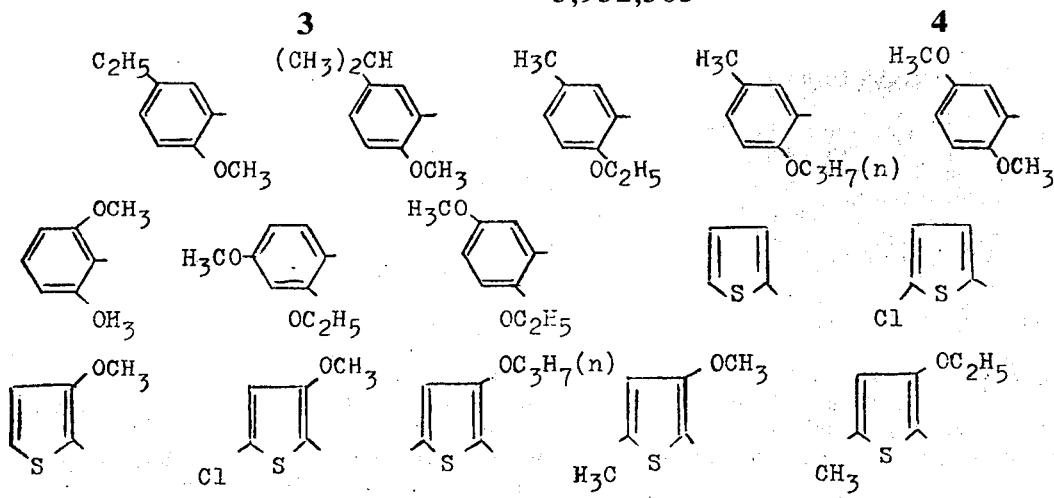

As examples for the bridge member Y there are mentioned:

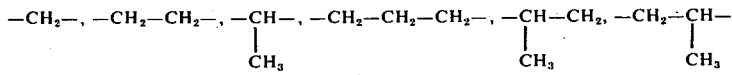

those binding the benzene nucleus with the carbonamido group over 2 carbon atoms being preferred.

The phenylene group mentioned in the formula by

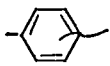

is preferably unsubstituted. It may, however, likewise be mono- or polysubstituted by halogen, lower alkyl or lower alkoxy. It may carry the other parts of the molecule in ortho-, meta- or para-position to each other, the para-position being preferred.

The products of the present invention may be prepared by methods well known in the benzene-sulfonylurea art, for example by reacting a benzene-sulfonyl-isocyanate, -carbamic acid ester, -thiol-carbamic acid ester, -carbamic acid halide or -urea substituted by the group
X-CO-NH-Y
with a $R^1$-substituted amine.

The reaction products are treated with alkaline agents, if the formation of salts is desired.

According to the nature of the starting substances in particular of the member X one or the other method for the preparation of certain individual compounds corresponding to the aforementioned general formula may be unsuitable in some cases, or, at least, require measures for the protection of active groups. Such cases which do not occur very often can easily be recognized by the expert and there will be no difficulty in applying in these cases another method of synthesis.

As regards the reaction conditions, the forms of realizing the process of the invention may, in general, vary within wide limits and can be adapted to each individual case. For example, the reactions can be carried out with the use of solvents either at room-temperature or at an elevated temperature.

The hypoglycemic action of the benzene-sulfonylurea derivatives described above could be determined by feeding them to rabbits for example in the form of sodium salt in doses of 10 mg/kg and determining the blood sugar value according to the known method by Hagedown-Jensen or by means of an auto-analyzer over a prolonged period of time.

Thus, it was found, for example, that 10 milligrams/kilogram of N-[4-($\beta$-<2-methoxy-5-fluoro-benzamido>-ethyl)-benzene-sulfonyl]-N'-(3,4-dimethyl-cyclohexyl)-urea provoke, after 3 hours, a lowering of the blood sugar by 45%, which, after 24 hours still amounts to 44% and which falls to zero only after 48 hours. In the same manner, 10 milligrams of N-[4-($\beta$-<2-methoxy-5-chlorobenzamido->-ethyl)-benzene-sulfonyl]-N'-(2,4-dimethyl-cyclohexyl)-urea provoke after 3 hours a blood sugar lowering of 31 %, which after 24 hours even amounts to 39%, 10 mg of N-[4-($\beta$-<2-methoxy-5-chloro-benzamido>-ethyl)-benzenesulfonyl]-N'-cyclopentyl-urea provoke after 3 hours a blood sugar lowering of 39%, which after 24 hours amounts to 45% and 10 mg of N-[4-($\beta$-<2-methoxy-5-chloro-benzamido>-ethyl)-benzenesulfonyl]-N'-(4-methyl-$\Delta$3-cyclohexenyl)-urea provoke after 3 hours a lowering of the blood sugar of 22 %, which, after 24 hours still amounts to 19 %, whereas the known N-[4-methyl-benzene-sulfonyl]-N'-butyl-urea, when administered to rabbits in doses of less than 25 mg/kg, does not provoke a lowering of the blood sugar level. The strong hypoglycemic action of the benzenesulfonylureas of the present invention becomes more evident if the dose is further reduced. When N-[4-($\beta$-<2-n-propoxy-benzamido>-ethyl)-benzenesulfonyl]-N'-(4,4-dimethyl-cyclohexyl)-urea is administered to rabbits in a dose of 0.02 mg/kg and N-[4-($\beta$-<2-methoxy-5-chloro-benzamido>-ethyl)-benzenesulfonyl]-N'-(3,4-dimethylcyclohexyl)-urea is administered to rabbits in a dose of 0.01 mg/kg, and the N-[4-($\beta$-<2-methoxy-5-fluorobenzamido>-ethyl)-benzenesulfonyl]-N'-(4,4-dimethyl-cyclohexyl) urea is administered to rabbits in a dose of 0.008 mg/kg, a distinct lowering of the blood sugar can still be observed.

Furthermore, it was found, that 10 mg/kg of N-[4-($\beta$-<2-ethoxy-5-fluoro-benzamido>-ethyl)-benzenesulfonyl]-N'-(4-chlorocyclohexyl)-urea provoke after 3 hours a lowering of the blood sugar of 39 %, which, after 24 hours still amounts to 28 % and after 48 hours to 16 %, and falls to zero only after 72 hours, that 10 mg/kg of N-[4-(β-<2-ethoxy-5-fluorobenzamido>-ethyl)-benzenesulfonyl]-N'-(3-methoxy-4-methylcyclohexyl)-urea provoke after 3 hours a lowering of the blood sugar of 32 %, which, after 24 hours still amounts to 21 % and falls to zero only after 48 hours.

10 mg/kg of N-[4-(β-<2-methoxy-5-chloro-benzamido>-ethyl)-benzene-sulfonyl]-N'-(4-chloro-cyclohexyl)-urea likewise provoke after 3 hours a lowering of the blood sugar of 25 % which, after 24 hours even amounts to 33 % and after 48 hours to 25 %.

10 mg/kg of N-[4-(β-<2-methoxy-5-chloro-benzamido>-ethyl)-benzenesulfonyl]-N'-(3-methoxy-4-methyl-cyclohexenyl)-urea provoke after 3 hours a lowering of the blood sugar of 25 %, which, after 24 hours amounts to 25% and after 48 hours still to 12 %. When N-[4-(β-<2-methoxybenzamido>-ethyl)-benzenesulfonyl]-N'-(4-chloro-cyclohexyl)-urea is administered to rabbits in a dose of 0.04 mg/kg, N-[4-(β-<2-methoxy-5-chlorobenzamido>-ethyl)benzenesulfonyl]-N'-(2-chloro-cyclohexyl)-urea is administered to rabbits in a dose of 0.04 mg/kg, N-[4-(β-<2-methoxy-5-chlorobenzamido>-ethyl)-benzenesulfonyl]-N'-(4-chloro-cyclohexyl)-urea is administered to rabbits in a dose of 0.02 mg/kg, N-[4-(β-<2-methoxy-5-chlorobenzamido>-ethyl)-benzenesulfonyl]-N'-(3-methoxy-4-methyl-cyclohexyl)-urea is administered in a dose of 0.1 mg/kg or N-[4-(β-<2-methoxy-5-methyl-benzamido>-ethyl)-benzenesulfonyl]-N'-(3-methoxy-4-methyl-cyclohexyl)-urea is administered to rabbits in a dose of 0.01 mg/kg, a distinct lowering of the blood sugar can still be observed.

As regards the toxicity of the compounds the values are within the same range as those of benzenesulfonyl-ureas, for example N-[4-methyl-benzenesulfonyl]-N'-n-butyl urea and N-[4-methyl-benzenesulfonyl]-N'-cyclohexyl-urea the $LD_{50}$ of which amounts to 2.5 and 4.8 grams/kg respectively, with oral application.

It results therefrom that the products of the invention show a very strong hypoglycemic action accompanied by a good tolerability.

The benzenesulfonyl-ureas of the present invention are preferably used for the manufacture of pharmaceutical preparations suitable for oral administration and for the lowering of the blood sugar level in the treatment of diabetes mellitus, for which purpose it may be used as such or in the form of its physiologically tolerable salts or in the presence of substances which cause salt formation. For the formation of salts, there may be used, for example, alkaline agents such as alkali metal or alkaline earth metal hydroxides, carbonates or bicarbonates.

The present invention therefore also provides pharmaceutical preparations that have hypoglycemic action and are suitable for oral administration in the treatment of diabetes mellitus, which preparations have preferably the form of tablets and contain as the active ingredient the benzenesulfonyl-ureas of the invention or a salt thereof in admixture or conjunction with pharmaceutically suitable carriers such as talc, starch, lactose, tragacanth or magnesium stearate.

Such a pharmaceutical preparation, for example a tablet or a powder, containing the benzenesulfonyl-ureas of the invention or a physiologically tolerable salt thereof as the active substance, with or without one or more of the aforementioned carriers, are advantageously brought into a suitable dosage unit form. The dose chosen should comply with the activity of the benzenesulfonyl-urea used and with the desired effect. Advantageously, the dosage per unit amounts to about 0.5 to 100 mg, preferably 2 to 10 mg, but considerably higher or lower dosage units may also be used, which, where required, are divided or multiplied prior to their administration.

The following Examples serve to illustrate some variants of the process, which may be used for the synthesis of the benzenesulfonyl-ureas of the invention.

EXAMPLE 1

N-[4-(β-<2-methoxy-5-chlorobenzamido>-ethyl)-benzenesulfonyl>-N'-(3-methoxy-4-methyl-cyclohexyl)-urea 4.2 g of N-[4-(β-<2-methoxy-5-chlorobenzamido>-ethyl)-benzenesulfonyl]-methyl-urethane (melting point 189°– 191°C) are suspended in 50 ml of dioxane and dissolved in 50 ml dioxane after addition of 2 g of 3-methoxy-4-methyl-cyclohexyl-amine-acetate (melting point 134°– 136° C) (obtained by hydrogenation of the nucleus of 3-methoxy-4-methylaniline at $Co_2O_3$ at 260°C and under a pressure of 250 atmospheres $H_2$) and heated for about 1 hour to 110°C, in which process the methanol which has formed during the reaction is distilled off. After cooling, water is added and the N-[4-(β-<2-methoxy-5-chlorobenzamido>-ethyl)-benzenesulfonyl]-N'-(3-methoxy-4-methylcyclohexyl)-urea precipitates in crystalline form and it is recrystallized from methanol (melting point 179° – 181° C). In analogous manner, there is obtained: from N-[4-(β-<3-trifluoromethylbenzamido>-ethyl)-benzenesulfonyl]-methylurethane (melting point 178° – 180°C)

N-[4-(β-<3-trifluoromethylbenzamido>-ethyl)-benzenesulfonyl]-N'-(3-methoxy-4-methylcyclohexyl)-urea, melting point 159° – 161°C (from methanol);

the N-[4-(β-<3-trifluoromethyl-benzamido>-ethyl)-benzenesulfonyl]-N'-(3-methyl-cyclopentyl)-urea, melting point 166° – 168°C (from methanol); from N-[4-(β-<3,4-dichloro-benzamido>-ethyl)-benzenesulfonyl]-methyl-urethane:

the N-[4-(β-<3,4-dichloro-benzamido>-ethyl)-benzenesulfonyl]-N'-(3-methyl-cyclopentyl)-urea, melting point 180° – 181°C (from methanol);

the N-[4-(β-<3,4-dichlorobenzamido>-ethyl)-benzenesulfonyl]-N'-cycloheptene-(2)-yl-urea, melting point 197° – 199°C from methanol/dimethylformamid);

from

N-[4-(β-<3,4-dichlorobenzamido>-ethyl)-benzenesulfonyl]-methylurethane (melting point 198°–200°C)

N-[4-(β-<3,4-dichlorobenzamido>-ethyl)-benzenesulfonyl]-N'-(3-methoxy-4-methylcyclohexyl)-urea, melting point 190° – 191°C (from methanol); from N-[4-(β-<3-benzyloxythiophencarbonamido>-ethyl)-benzenesulfonyl]-methylurethane (melting point 163°– 164°C), the N-[4-(β-<3-benzyloxythiophene-2-carbonamido>-ethyl)-benzenesulfonyl]-N'-(3-methoxy-4-methyl-cyclohexyl)-urea, melting point 177° – 178°C (from methanol); from N-[4-(β-<3-ethoxythiophen-2-carbonamido>-ethyl)-benzenesulfonyl]-methylurethane (melting point 163° – 165°C), the N-[4-(β-<3-ethoxythiophen-2-carbonamido>-ethyl)-benzenesulfonyl]-

N'-(3-methoxy-4-methylcyclohexyl)-urea, melting point 154° – 156°C (from methanol);

from
N-[4-(β-<2-methoxybenzamido>-ethyl)-benzenesulfonyl]-methylurethane (melting point 174° – 176°C), the
N-[4-(β-<2-methoxybenzamido>-ethyl)-benzenesulfonyl]-N'-(3-methoxy-4-methylcyclohexyl)-urea, melting point 184° – 185°C (from methanol);

the N-[4-(β-<2-methoxy-benzamido>-ethyl)-benzenesulfonyl]-N'-cyclo-octene-(2)-yl-urea, melting point 168° – 170°C (from methanol);

N-[4-(β-2-methoxy-benzamidoethyl)-benzenesulfonyl]-N'-(3-methyl-Δ2-cyclopentenyl)-urea (melting point 145° – 147°C), N-[4-(β-2-methoxy-benzamidoethyl)-benzenesulfonyl]-N'-(2,3,4,4-tetramethyl-cyclopentyl)-urea (melting point 147°–149°C), N-[4-(β-2-methoxy-benzamidoethyl)-benzenesulfonyl]-N'-(3,3,4-trimethyl-cyclopentyl)-urea (melting point 164° – 166°C), N-[4-(β-2-methoxy-benzamidoethyl)-benzenesulfonyl]-N'-(3,4,4-trimethyl-Δ2-cyclopentenyl)-urea (melting point 94°C), N-[4-(β-2-methoxy-benzamidoethyl)-benzenesulfonyl]-N'-(3,3-dimethylcyclopentyl)-urea (melting point 173° – 174,5°C), the N-[4-(β-<2-methoxy-benzamido>-ethyl)-benzenesulfonyl]-N'-(2-chloro-cyclopentyl)-urea, melting point 182° – 183°C (from methanol);

the N-[4-(β-<2-methoxy-benzamido>-ethyl)-benzenesulfonyl]-N'-(3-tert.butyl-cyclopentyl)-urea, melting point 175° – 177°C (from methanol);

the N-[4-(β-<2-methoxy-benzamido>-ethyl)-benzenesulfonyl]-N'-(3-methyl-cyclopentyl)-urea, melting point 164° – 165°C (from methanol);

from N-[4-(β-<2-ethoxy-benzamido>-ethyl)-benzenesulfonyl]-methyl-urethane:

the N-[4-(β-<2-ethoxy-benzamido>-ethyl)-benzenesulfonyl]-N'-(3-methyl-cyclopentyl)-urea, melting point 139°–141°C (from methanol);

the N-[4-(β-<2-ethoxy-benzamido>-ethyl)-benzenesulfonyl]-N'-(4,4-dimethylcyclohexene-(2)-yl)-urea, melting point 141° – 142°C (from methanol); and the N-[4-(β-<2-ethoxy-benzamido>-ethyl)-benzenesulfonyl]-N'-cycloheptene-(2)-yl-urea, melting point 162°–164°C (from methanol);

from
N-[4-(β-<2-methoxy-4-chlorobenzamido>-ethyl)-benzenesulfonyl]-methylurethane (melting point 178° – 180°C), the N-[4-(β-<2-methoxy-4-chlorobenzamido>-ethyl)-benzenesulfonyl]-N'-(3-methoxy-4-methylcyclohexyl)-urea, melting point 191° – 193°C (from methanol);

N-]4-(β-(2-methoxy-4-chlorobenzamido>-ethyl)-benzenesulfonyl]-N'-(3,3-dimethylcyclopentyl)-urea (melting point 195°-196°C);

from
N-[4-(β-<2-methoxy-5-methylbenzamido>-ethyl)-benzenesulfonyl]-methylurethane, (melting point 175°-177°C), the N-[4-(β-<2-methoxy-5-methyl-benzamido>-ethyl)-benzenesulfonyl]-N'-(3-methoxy-4-methylcyclohexyl)-urea, melting point 177° – 179°C (from methanol/dimethylformamide);

from
N-[4-(β-<2-methoxy-5-bromobenzamido>-ethyl)-benzenesulfonyl]-methylurethane, (melting point 197° – 199°C), the N-[4-(β-<2-methoxy-5-bromobenzamido>-ethyl)-benzenesulfonyl]-N'-(3-methoxy-4-methylcyclohexyl)-urea, melting point 181° – 183°C (from methanol/dimethylformamide);

from
N-[4-(β-<3,5-dimethylbenzamido>-ethyl)-benzenesulfonyl]-methylurethane (melting point 223° – 225°C), the N-[4-(β-<3,5-dimethylbenzamido>-ethyl)-benzenesulfonyl]-N'-(3-methoxy-4-methoxy-4-methylcyclohexyl)-urea, melting point 181° – 183° C (from methanol);

the N-[4-(β-<3,5-methylbenzamido>-ethyl)-benzenesulfonyl]-N'-(2-chlorocyclopentyl)-urea, melting point 207° – 209° C (from methanol);

the N-[4-(β-<3,5-dimethylbenzamido>-ethyl)-benzenesulfonyl]-N'-(3-tert.butyl-cyclopentyl)-urea, melting point 150° – 152° C (from methanol);

the N-[4-(β-<3,5-dimethylbenzamido>-ethyl)-benzenesulfonyl]N'-(3-methyl-cyclopentyl)-urea, melting point 183° – 185°C (from methanol);

from
N-[4-(β-<2-allyloxy-5-chlorobenzamido>-ethyl)-benzenesulfonyl]-methylurethane (melting point 167° – 169°C), the
N-[4-β-<2-allyloxy-5-chlorobenzamido>-ethyl)-benzenesulfonyl]-N'-(3-methoxy-4-methylcyclohexyl)-urea, melting point 146° – 148°C (from methanol);

from
N-[4-(β-<2-ethoxy-5-fluorobenzamido>-ethyl)-benzenesulfonyl]-methylurethane (melting point 193° – 195°C), the N-[4-9β-<2-ethoxy-5-fluorobenzamido>-ethyl)-benzenesulfonyl]-N'-(3-methoxy-4-methylcyclohexyl)-urea, melting point 173° – 174°C (from methanol);

the N-[4-(β-<2-ethoxy-5-fluorobenzamido>-ethyl)-benzenesulfonyl]-N'-(4,4-dimethyl-cyclohexene-(2)-yl)-urea, melting point 140° – 141°C (from methanol); from N-[4-(β<2-ethoxy-5-chloro-benzamido>-ethyl)-benzenesulfonyl]-methyl-urethane:

the N-[4-(β-<2-ethoxy-5-chloro-benzamido>-ethyl)-benzenesulfonyl]-N'-(3-tert.butyl-cyclopentyl)-urea, melting point 152° – 153° C (from methanol);

the N-[4-(β-<2-ethoxy-5-chloro-benzamido>-ethyl-benzenesulfonyl]-N'-(3-methyl-cyclopentyl)-urea, melting point 144° – 146°C (from methanol); from N-[4-(β-<2-ethoxy-4-trifluoromethylbenzamido>-ethyl)-benzenesulfonyl]-methylurethane (melting point 166° – 168°C), the N-[4-(β-<2-ethoxy-4-trifluoromethylbenzamido>-ethyl)-benzenesulfonyl]-N'-(3-methoxy-4-methylcyclohexyl)-urea, melting point 171° – 173° C (from methanol); from N-[4-(β-tetraline-(2)-carbamido)-ethyl]-benzenesulfonylmethylurethane (melting point 176°C), the N-]4-(β-tetraline-(2)-carbamidoethyl)-benzenesulfonyl]-N'-(3-ethoxy-4-methylcyclohexyl)-urea, melting point 138°C (from methanol/water).

EXAMPLE 2

N-]4-(β-<2-methoxy-5-methylbenzamido>-ethyl)-benzenesulfonyl]-N'-(3-ethoxy-4-methyl-cyclohexyl)-urea 4 g of N-[4-(β-<2-methoxy-5-methylbenzamido>-ethyl)-benzenesulfonyl]-methyl-urethane (melting point 175° – 177°C) are suspended in 75 ml of dioxane and 1.7 g of 3-ethoxy-4-methyl-cyclohexylamine (boiling at 80°C under a pressure of 10 mm of mercury) obtained by hydrogenation of the nucleus of 3-ethoxy-4-methylaniline at $Co_2O_3$ at 260° C and 250 atmospheres $H_2$) are added. The whole is heated for 1 hour to 110°C. Then the N-[4-(β-<2-methoxy-5-methylbenzamido>-ethyl)-benzenesulfonyl]-N'-(3-ethoxy-4-methyl-cyclohexyl)-urea is precipitated by means of water. The cristals melt after recrystallization from methanol at 172°–174°C.

In analogous manner, there is obtained: from
N-[4-(β-<3-chlorobenzamido>-ethyl)-benzenesulfonyl]-methylurethane (melting point 173°–175°C), the
N-[4-(β-<3-chlorobenzamido>-ethyl)-benzenesulfonyl]-N'-(3-ethoxy-4-methylcyclohexyl)-urea, melting point 178° – 180°C);
the N-[4-(β-<3-chlorobenzamido>-ethyl)-benzenesulfonyl]-N'-cyclopentene-(2)-yl-urea, melting point 195° – 196°C (from methanol);
the N-[4-(β<3-chlorobenzamido>-ethyl)-benzenesulfonyl]-N'-(4,4-dimethylcyclohexene-(2)-yl)-urea, melting point 188° – 190° C (from methanol);
the N-[4-(β-<3-chlorobenzamido>-ethyl)-benzenesulfonyl]-N'-cycloheptene-(2)-yl-urea, melting point 170° – 172°C (from methanol) and the N-[4-(β-<3-chlorobenzamido>-ethyl)-benzenesulfonyl]-N'-cyclo-octene-(2)-yl-urea, melting point 179° – 181° C (from methanol);
N-[4-(β-<3-chlorobenzamido>-ethyl)-benzenesulfonyl]-N'-(3,3-dimethylcyclopentyl)-urea, melting point 162° – 164°C;
N-[4-(β-<3-chlorobenzamido>-ethyl)-benzenesulfonyl]-N'-(3-methyl-Δ2-cyclopentenyl)-urea, melting point 159° – 160°C;
N-[4-(β-<3-chlorobenzamido>-ethyl)-benzenesulfonyl]-N'-(3,3,4-trimethylcyclopentyl)-urea, melting point 137°–139°C;
the N-[4-(β-<3-chlorobenzamido>-ethyl)-benzenesulfonyl]-N'-(2-chloro-cyclopentyl)-urea, melting point 192° – 193°C (methanol);
the N-[4-(β-<3-chlorobenzamido>-ethyl)-benzenesulfonyl]-N'-(1-methyl-cyclopentyl)-urea, melting point 191°–193° C (from methanol);
the N-[4-(β-<3-chlorobenzamido>-ethyl)-benzenesulfonyl]-N'-(3-tert.butyl-cyclopentyl)-urea, melting point 174°–175° C (from methanol);
the N-[4-(β-<3-chlorobenzamido>-ethyl)-benzenesulfonyl]-N'-(3-methyl-cyclopentyl)-urea, melting point 164° – 166° C (from methanol); from
N-[4-(β<3-methoxythiophene-2-carbonamido>-ethyl)-benzenesulfonyl]-methylurethane (melting point 226° – 228° C);
N-[4-(β-<3-methoxythiophene-2-carbonamido>-ethyl)-benzenesulfonyl]-N'-(3-ethoxy-4-methylcyclohexyl)-urea, melting point 157° – 159° C (from methanol);
N-[4-(β<-3-methoxythiophen-2-carbonamido>-ethyl)-benzenesulfonyl]-N'-cyclopentene-2-yl-urea, melting point 204° – 205° C (from methanol);
N-[4-(β<-3-methoxy-thiophen-2-carbonamido>ethyl)-benzenesulfonyl]-N'-(3-methyl-Δ2-cyclopentenyl)-urea, melting point 163° – 164.5° C;
N-[4-(β<-3-methoxy-thiophen-2-carbonamido>ethyl)-benzenesulfonyl]-N'-(3,3,4-trimethylcyclopentyl)-urea, melting point 180° – 182°C;
N-[4-(β<-3-methoxy-thiophen-2-carbonamido>ethyl)-benzenesulfonyl]-N'-(3-tert.butylcyclopentyl)-urea, melting point 191°–193° C;
N-[4-(β-<3-methoxy-thiophen-2-carbonamido>ethyl)-benzenesulfonyl]-N'-(3-ethylcyclopentyl)-urea, melting point 173°–175°C;
N-[4-(β-<3-methoxy-thiophen-2-carbonamido>ethyl)-benzenesulfonyl]-N'-(3,3-dimethylcyclopentyl)-urea, melting point 190° – 192° C;
the N-[4-(β-<3-methoxy-thiophen-2-carbonamido>-ethyl)-benzenesulfonyl]-N'-(3-methyl-cyclopentyl)-urea, melting point 178° – 179° C; from
N-[4-β-<3-ethoxythiophen-2-carbonamido>-ethyl)-benzenesulfonyl]-methyl-urethane (melting point 163°–165°C):
N-[4-β-<3-ethoxythiophen-2-carbonamido>-ethyl)-benzenesulfonyl]-N'-(4,4-dimethylcyclohexene-2-yl)-urea, melting point 140° – 142° C (from methanol);
N-[4-(β-<3-ethoxy-thiophen-2-carbonamido>-ethyl)-benzenesulfonyl]-N'-(3,3-dimethylcyclopentyl)-urea, melting point 162° – 164° C; from
N-[4-(β-<2-methoxybenzamido>-ethyl)-benzenesulfonyl]-methylurethane (melting Point 174° – 176° C);
N-[4-(β-<2-methoxybenzamido>-ethyl)-benzenesulfonyl]-N'-(3-ethoxy-4-methylcyclohexyl)-urea, melting point 168° – 169°C (from methanol);
N-[4-(β-<2-methoxy-benzamido>-ethyl)-benzenesulfonyl]-N'-cyclopentene-2-yl-urea, melting point 170° – 172°C (from methanol);
N-[4-(β-<2-methoxy-benzamido>-ethyl)-benzenesulfonyl]-N'-(4,4-dimethylcyclohexene-2-yl)-urea, melting point 178° – 179°C (from methanol);
N-[4-(β-<2-methoxy-benzamido>-ethyl)-benzenesulfonyl]-N'-cycloheptene-(2)-yl-urea, melting point 174° – 176° C (from methanol); from
N-[4-(β-<2-n-butoxybenzamido>-ethyl)-benzenesulfonyl]-methylurethane (melting point 160° – 162°C);
N-[4-(β-<2-n-butoxybenzamido>-ethyl)-benzenesulfonyl]-N'-(3-ethoxy-4-methylcyclohexyl)-urea, melting point 140° – 142°C (from methanol); from
N-[4-(β-<2-methoxy-5-chlorobenzamido>-ethyl)-benzenesulfonyl]-methylurethane (melting point 189° – 191° C);
N-[4-(β-<2-methoxy-5-chlorobenzamido>-ethyl)-benzenesulfonyl]-N'-(3-ethoxy-4-methylcyclohexyl)-urea, melting point 173° – 175°C (from methanol);
the N-[4-(β-<2-methoxy-5-chlorobenzamido>-ethyl)-benzenesulfonyl]-N'-cyclopentene (2)-yl-urea, melting point 188° – 189° C (from methanol);
the N-[4-(β-<2-methoxy-5-chlorobenzamido>-ethyl)-benzenesulfonyl]-N'-(4,4-dimethylcyclohexene-(2)-yl)-urea, melting point 170°–172° C (from methanol);

the N-[4-(β-<2-methoxy-5-chlorobenzamido>-ethyl)-benzenesulfonyl]-N'-cycloheptene-(2)-yl-urea, melting point 142° – 144°C (from methanol); and the N-[4-(β-<2-methoxy-5-chlorobenzamido>-ethyl)-benzenesulfonyl]-N'-cyclooctene-(2)-yl-urea, melting point 171° – 172°C (from methanol);

N-[4-(β-<2-methoxy-5-chlorobenzamido>-ethyl)-benzenesulfonyl]-N'-(3,4,4-trimethyl-Δ2-cyclopentenyl)-urea, melting point 152° – 155°C;

N-[4-(β-<2-methoxy-5-chlorobenzamido>-ethyl)-benzenesulfonyl]-N'-(3-ethyl-cyclopentyl)-urea, melting point 117° – 119° C;

N-[4-(β-<2-methoxy-5-chlorobenzamido>-ethyl)-benzenesulfonyl]-N' -(3-methyl-Δ2-cyclopentenyl)-urea, melting point 159° – 161°C;

N-[4-(β-<2-methoxy-5-chlorobenzamido>-ethyl)-benzenesulfonyl]-N'-(2,3,4,4-tetramethyl-cyclopentyl)-urea, melting point 172° – 174° C;

N-[4-(β-<2-methoxy-5-chlorobenzamido>-ethyl)-benzenesulfonyl]-N'-(3,3-dimethyl-cyclopentyl)-urea, melting point 164° – 165°C;

N-[4-(β-<2-methoxy-5-chlorobenzamido>-ethyl)-benzenesulfonyl]-N'-(3,3,4-trimethylcyclopentyl)-urea, melting point 169°–171°C; from N-[4-(β-<3,5-dimethylbenzamido>-ethyl)-benzenesulfonyl]-methylurethane (melting point 223° – 225°C);

N-[4-(β-<3,5-dimethylbenzamido>-ethyl)-benzenesulfonyl]-N'-(3-ethoxy-4-methylcyclohexyl)-urea, melting point 190° – 192°C (from methanol);

the N-[4-(β-<3,5-dimethyl-benzamido>-ethyl)-benzenesulfonyl]-N'-cycloheptene-(2)-yl-urea, melting point 196° – 198° C (from methanol);

N-[4-(β-<3,5-dimethyl-benzamido>-ethyl)-benzenesulfonyl]-N'-(3-methyl-Δ2-cyclopentenyl)-urea, melting point 187° – 188°C;

N-[4-(β-<3,5-dimethyl-benzamido>-ethyl)-benzenesulfonyl]-N'-(3,3-dimethylcyclopentyl)-urea, melting point 201° – 203°C; from N-[4-(β-<2-methoxyethoxy-benzamido>-ethyl)-benzenesulfonyl]-methylurethane (melting point 123° – 125°C):

the N-[4-(β-<2-methoxyethoxy-benzamido>-ethyl)-benzenesulfonyl]-N'-(4,4-dimethylcyclohexene-(2)-yl)-urea, melting point 153° – 155° C (from methanol); and the N-[4-(β-<2-methoxy-ethoxy-benzamido>-ethyl)-benzenesulfonyl]-N'-cycloheptene-(2)-yl-urea, melting point 166° – 168° C (from methanol); from N-[4-(β-<2-methoxymethoxy-benzamido>-ethyl)-benzenesulfonyl]-methyl-urethane:

the N-[4-(β-<2-methoxymethoxy-benzamido>-ethyl)-benzenesulfonyl]-N'-(3-methyl-cyclopentyl)-urea, melting point 147° – 149° C (from methanol); from N-[4-(β-<2-ethoxy-5-acetylbenzamido>-ethyl)-benzenesulfonyl]-methylurethane (melting point 164° – 166°C):

N-[4-(β-<2-ethoxy-5-acetylbenzamido>-ethyl)-benzenesulfonyl]-N'-(3-ethoxy-4-methylcyclohexyl)-urea, melting point 155° 157°C (from methanol); from N-[4-9β-<3-methoxy-5-chlorothiophen-2-carbonamido>-ethyl)-benzenesulfonyl]-methylurethane (melting point 186° – 188°C):

the N-[4-(β-<3-methoxy-5-chlorothiophen-2-carbonamido>-ethyl) -benzenesulfonyl]-N'-cycloheptene-(2)-yl-urea, melting point 164° – 166° C (from methanol);

the N-[4-(β-<3-methoxy-5-chloro-thiophen-2-carbonamido>-ethyl) -benzenesulfonyl]-N'-(3-methyl-cyclopentyl)-urea, melting point 169° – 170° C (from methanol);

N-[4-(β-<3-methoxy-5-chloro-thiophen-2-carbonamido>ethyl)-benzenesulfonyl]-N'-(3-ethyl-cyclopentyl)-urea, melting point 174° – 176° C;

N-[4-(β-<3-methoxy-5-chloro-thiophen-2-carbonamido>-ethyl)-benzenesulfonyl]-N'-(3-tert.-butylcyclopentyl)-urea, melting point 163° – 165° C;

N-[4-(β-<3-methoxy-5-chloro-thiophen-2-carbonamido>-ethyl)-benzenesulfonyl]-N'-(3,3,4-trimethyl-cyclopentyl)-urea, melting point 156° – 158° C; from N-[4-(β-<2-methoxy-5-methylbenzamido>-ethyl)-benzenesulfonyl]-methylurethane (melting point 175° – 177°C):

N-[4-(β-<2-methoxy-5-methylbenzamido>-ethyl)-benzenesulfonyl]-N'-(3-methyl-4-methoxycyclohexyl)-urea, melting point 110°–112° C (from methanol);

the N-[4-(β-<2-methoxy-5-methyl-benzamido>-ethyl)-benzenesulfonyl]-N'-(5-methyl-cyclohexene-(2)-yl)-urea, melting point 171° – 173° C (from methanol);

the N-[4-(β->2-methoxy-5-methyl-benzamido>-ethyl)-benzenesulfonyl]-N'-(3-tert. butyl-cyclopentyl)-urea, melting point 143° – 145° C (from methanol);

the N-[4-(β-<2-methoxy-5-methyl-benzamido>-ethyl)-benzenesulfonyl]-N'-(3-methyl-cyclopentyl)-urea, melting point 151° – 153°C (from methanol);

N-[4-(β-<2-methoxy-5-methyl-benzamido>-ethyl)-benzenesulfonyl]-N'-(3,4,4-trimethyl-Δ2-cyclopentenyl)-urea, melting point 90°C;

N-[4-(β-<2-methoxy-5-methyl-benzamido>ethyl)-benzenesulfonyl]-N'-(3-ethyl-cyclopentyl)-urea, melting point 131° – 133°C;

N-[4-(β-<2-methoxy-5-methyl-benzamido>ethyl)-benzenesulfonyl]-N'-(3,3-dimethyl-cyclopentyl)-urea, melting point 150°–151°C;

N-[4-(β-<2-methoxy-5-methyl-benzamido>ethyl)-benzenesulfonyl]-N'-(3,3,4-trimethylcyclopentyl)-urea, melting point 152°–153°C;

N-[4-(β-2->methoxy-5-methyl-benzamido>-ethyl)-benzenesulfonyl]-N'-(3-methyl-Δ2-cyclopentenyl)-urea, melting point 149°–151°C; N-[4-(β-<2-methoxy-5-methyl-benzamido>-ethyl)-benzenesulfonyl]-N'-(2,3,4,4-tetramethyl-cyclopentyl)-urea, melting point 153° – 155°C;

the N-[4-(β-<2-methoxy-5-methyl-benzamido>-ethyl)-benzenesulfonyl]-N'-(2-chloro-cyclopentyl)-urea, melting point 209°–210°C (from methanol/dimethylformamide/water);

the N-[4-(β-<2-methoxy-5-methyl-benzamido>-ethyl)-benzenesulfonyl]-N'-(1-methyl-cyclopentyl)-urea, melting point 156°–158° C (from methanol);

the N-[4-(β-<2-methoxy-5-methylbenzamido>-ethyl)-benzenesulfonyl]-N'-cyclopentene-(2)-yl-urea, melting point 201° – 203°C (from methanol/dimethylformamide);

the N-[4-(β-<2-methoxy-5-methylbenzamido>-ethyl)-benzenesulfonyl]-N'-(4,4-dimethyl-cyclohexene-(2)-yl)-urea, melting point 152° – 154°C (from methanol);

the N-[4-(β-<2-methoxy-5-methyl-benzamido>-ethyl)-benzenesulfonyl]-N'-cycloheptene-(2)-yl-urea, melting point 177° – 178° C (from methanol); and the N-[4-(β-<2-methoxy-5-methylbenzamido>-ethyl)-benzenesulfonyl]-N'-cyclooctene-(2)-yl-urea, melting point 178° – 180°C (from methanol/dimethylformamide); from N-[4-(β-<2-methoxy-5-bromobenzamido>-ethyl)-benzenesulfonyl]-methylurethane (melting point 197° – 199° C):

N-[4-(β-<2-methoxy-5-bromo-benzamido>-ethyl)-benzenesulfonyl]-N'-(3-ethoxy-4-methylcyclohexyl)-urea, melting point 178° – 180° C (from methanol);

N-[4-(β-<2-methoxy-5-bromo-benzamido>-ethyl)-benzenesulfonyl]-N'-(3-ethyl-cyclopentyl)-urea, melting point 146° – 147° C;

N-[4-(β-<2-methoxy-5-bromo-benzamido>-ethyl)-benzenesulfonyl]N'-(3,3-dimethyl-cyclopentyl)-urea, melting point 153° – 155°C;

N-[4-(β-<2-methoxy-5-bromo-benzamido>-ethyl)-benzenesulfonyl]-N'-(3-methyl-Δ2-cyclopentenyl)-urea, melting point 153°–155°C;

N-[4-(β-<2-methoxy-5-bromo-benzamido>ethyl)-benzenesulfonyl]-N'-(2,3,4,5-tetramethylcyclopentyl)-urea, melting point 168°–170°C;

N-[4-9β-<2-methoxy-5-bromo-benzamido>-ethyl)-benzenesulfonyl]-N'-(3,3,4-trimethyl-cyclopentyl)-urea, melting point 154° – 156° C;

the N-[4-(β-<2-methoxy-5-bromo-benzamido>-ethyl)-benzenesulfonyl]-N'-(2-chloro-cyclopentyl)-urea, melting point 191° – 193° C (from methanol/dimethylformamide);

the N-[4-(β-<2-methoxy-5-bromo-benzamido>-ethyl)-benzenesulfonyl]-N-(3-tert.butyl-cyclopentyl)-urea, melting point 144° – 146° C (from methanol);

the N-[4-(β-<2-methoxy-5-bromo-benzamido>-ethyl)-benzenesulfonyl]-N'-(3-methyl-cyclopentyl)-urea, melting point 144° – 145°C;

N-[4-(β-<2-methoxy-5-bromobenzamido>-ethyl)-benzenesulfonyl]-N'-(3-methyl-4-methoxycyclohexyl)-urea, melting point 113°C (decomposition) (from methanol);

the N-[4-(β-<2-methoxy-5-bromobenzamido>-ethyl)-benzenesulfonyl]-N'-cyclopentene-(2)-yl-urea, melting point 188° – 190°C (from methanol);

the N-[4-(β-<2-methoxy-5-bromobenzamido>-ethyl)-benzenesulfonyl]-N'-(4,4-dimethylcyclohexene-(2)-yl-urea, melting point 118° – 120° C (from methanol);

the N-[4-(β-<2-methoxy-5-bromobenzamido>-ethyl)-benzenesulfonyl]-N'-cycloheptene-(2)-yl-urea, melting point 142° – 144°C (from methanol); and the N-[4-(β-<2-methoxy-5-bromobenzamido>ethyl)-benzenesulfonyl]-N'-cyclooctene-(2)-yl-urea, melting point 175° – 176° C (from methanol); from N-[4-(β-<2-methoxy-5-chlorobenzamido>-ethyl)-benzenesulfonyl]-methyl-urethane:

the N-[4-(β-<2-methoxy-5-chlorobenzamido>-ethyl)-benzenesulfonyl]-N'-(2-chloro-cyclopentyl)-urea, melting point 196° – 198° C (from methanol);

the N-[4-(β-<2-methoxy-5-chlorobenzamido>-ethyl)-benzenesulfonyl]-N'-(1-methyl-cyclopentyl)-urea, melting point 171° – 173° C (from methanol);

the N-[4-(β-<2-methoxy-5-chlorobenzamido>-ethyl)-benzenesulfonyl]-N'-(5-methyl-cyclohexene-(2)-yl)-urea, melting point 173° – 175° C (from methanol);

the N-[4-(β-<2-methoxy-5-chlorobenzamido>-ethyl)-benzenesulfonyl]-N'-(3-tert.butyl-cyclopentyl)-urea, melting point 140° – 142° C (from methanol);

the N-[4-(β-<2-methoxy-5-chlorobenzamido>-ethyl)-benzenesulfonyl]-N'-(3-methyl-cyclopentyl)-urea, melting point 152° – 153° C (from isopropanol);

N-[4-(β-<2-methoxy-5-chlorobenzamido>-ethyl)-benzenesulfonyl]-N'-(3-methyl-4-methoxycyclohexyl)-urea, melting point 112° – 114° C (decomposition) (from methanol);

N-[4-(β-<2-methoxy-5-chlorobenzamido>-ethyl)-benzenesulfonyl]-N'-cyclopentyl-urea, melting point 184° – 185°C (from methanol); from N-[4-(β-<3-chlorobenzamido>-ethyl)-benzenesulfonyl]-methylurethane (melting point 173° – 185°C):

N-[4-(β-<3-chlorobenzamido>-ethyl)-benzenesulfonyl]-N'-(3-methyl—-4-methoxycyclohexyl)-urea, melting point 166° 168° (from methanol).

EXAMPLE 3

N-[4-(β-<2-methoxy-5-chlorobenzamido>-ethyl)-benzenesulfonyl]-N'-cyclopentyl-urea 2.45 g of N-[4-(β-<2-methoxy-5-chlorobenzamido>-ethyl)-benzenesulfonyl]-phenylurethane (obtained from 4-[β-(2-methoxy-5-chlorobenzamido)-ethyl]-benzenesulfonamide and chloroformic acid phenyl ester) were refluxed for 2 hours with 0.43 g of cyclopentyl-amine in 30 ml of dioxane. After dilution with water and acidification with dilute hydrochloric acid a precipitate was obtained which was treated with 0.5 % ammonia. The aqueous alkaline solution was acidified and the precipitate obtained was recrystallized from methanol. N-[4-(β-<2-methoxy-5-chlorobenzamido>-ethyl)-benzenesulfonyl]-N'-cyclopentyl-urea, melting point 184° – 185° C, was obtained.

EXAMPLE 4

N-[4-(β-<3-methoxy-methoxythiophen-2-carbonamido>-ethyl)-benzenesulfonyl]-N'-(3-methoxy-4-methylcyclohexyl)-urea 5 g of 4-(β-<3-methoxy-methoxy-thiophen-2-carbonamido>-ethyl)-benzenesulfonamide (melting point 160° – 162°C) were dissolved in 7 ml of 2N sodium hydroxide solution and 50 ml of acetone and 2.4 g of 3-methoxy-4-methylcyclohexyl-isocyanate (boiling at 90°C under a pressure of 10 mm of mercury) were added dropwise at 0° – 5° C. Then stirring was continued for 2 hours, then the whole was diluted with water, and any undissolved matter was filtered off, and the filtrate was acidified with dilute hydrochloric acid. The N-[4-(β-<3-methoxy-methoxy-thiophen-2-carbonamido>-ethyl)-benzenesulfonyl]-N'-(3-methoxy-4-methyl-cyclohexyl)-urea precipitating in crystalline form melted at 125° – 127° C after recrystallization from methanol.

In analogous manner there were obtained: from
4-(β-<4-chlorobenzamido>-ethyl)-benzenesulfonamide (melting point 225° – 226°C):
N-[4-(β-<4-chlorobenzamido>-ethyl)-benzenesulfonyl]-N'-(3-methoxy-4-methylcyclohexyl)-urea, melting point 209° – 210°C (from methanol/dimethyl formamide);
N-[4-(β-<4-chlorobenzamido>-ethyl)-benzenesulfonyl]-N'-(3,3,4-trimethyl-cyclopentyl)-urea, melting point 174° – 176°C; from
4-(β-<3-methylbenzamido>-ethyl)-benzenesulfonamide (melting point 197° – 199°C):
N-[4-(β-<3-methylbenzamido>-ethyl)-benzenesulfonyl]-N'-(3-methoxy-4-methylcyclohexyl)-urea, melting point 167° – 169°C (from methanol); from
4-(β-<3,5-dimethylthiophen-2-carbonamido>-ethyl)-benzenesulfonamide (melting point 176° – 177°C): the N-[4-(β-<3,5-dimethylthiophen-2-carbonamido>-ethyl)-benzenesulfonyl]-N'-cycloheptene-(2)-yl-urea, melting point 184° – 185° C (from methanol); from
4-(β-<3-chlorothiophen-2-carbonamido>-ethyl)-benzenesulfonnamide (melting point 190° – 191° C):
the N-[4-(β-<3-chlorothiophen-2-carbonamido>-ethyl)-benzenesulfonyl]-N'-cycloheptene-(2)-yl-urea, melting point 190° – 191° C (from methanol/dimethylformamide); from
4-(β-<2-methoxymethoxy-benzamido>-ethyl)-benzenesulfonamide (melting point 169° – 170°C):
the N-[4-(β-<2-methoxymethoxy-benzamido>-ethyl)-benzenesulfonyl]-N'-cycloheptene-(2)-yl-urea, melting point 163° – 164° C (from methanol); from
4-(β-<2-methoxy-5-fluorobenzamido>-ethyl)-benzenesulfonamide (melting point 167° – 169°C):
the N-[4-(β-<2-methoxy-5-fluorobenzamido>-ethyl)-benzenesulfonyl]-N'-cycloheptene-(2)-yl-urea, melting point 157° – 159°C (from methanol); from
4-(β-<2-ethoxy-5-methylbenzamido>-ethyl)-benzenesulfonamide (melting point 147° – 148° C):
the N-[4-(β-<2-ethoxy-5-methylbenzamido>-ethyl)-benzenesulfonyl]-N'-cycloheptene-(2)-yl-urea, melting point 164° – 166°C (from methanol/dimethylformamide); from
4-(β-<3,4-tetramethylenethiophen-2-carbonamido>-ethyl)-benzenesulfonamide (melting point 173° – 174 ° C):
N-[4-(β-<3,4-tetramethylene-thiophen-2-carbonamido>-ethyl)-benzenesulfonyl]-N'-(3-methoxy-4-methylcyclohexyl)-urea, melting point 187° – 188° C (from methanol); from
4-(β-<2-methoxy-5-phenylbenzamido>-ethyl)-benzenesulfonamide (melting point 213° – 214°C):
N-[4-(β-<2-methoxy-5-phenylbenzamido>-ethyl)-benzenesulfonyl]-N'-(3-methoxy-4-methylcyclohexyl)-urea, melting point 143° – 145° C (from methanol); from
4-(β-<2-phenoxybenzamido>-ethyl)-benzenesulfonamide (melting point 187° – 188°C): N-[4-(β<2-phenoxybenzamido>-ethyl)-benzenesulfonyl]-N'-(3-methoxy-4-methylcyclohexyl)-urea, melting point 170° – 172°C (from methanol); from
4-(β-<2-methoxy-5-acetylbenzamido>-ethyl)-benzenesulfonamide (melting point 206° – 208° C):
N-[4-(β-<2-methoxy-5-acetylbenzamido>-ethyl)-benzenesulfonyl]-N'-(3-methoxy-4-methylcyclohexyl)-urea, melting point 174° – 176° C (from methanol/dimethylformamide);

EXAMPLE 5

N-[4-(β-<2-methoxy-5-chlorobenzamido>-ethyl)-benzenesulfonyl]-N'-(3-methoxy-4-methylcyclohexyl)-urea 3.9 g of 4-(β-<2-methoxy-4-chlorobenzamido>-ethyl)-benzenesulfonamide sodium and 6.7 g of N-N-diphenyl-N'-(3-methoxy-4-methylcyclohexyl)-urea (melting point 125° – 126°C) are heated to 110°C for 45 minutes in 100 ml of dimethylformamide. Then the whole is cooled, poured into water and ammonia of 1 % strenght is added. Then it is filtered off, the filtrate is acidified and the precipitate obtained is once more purified over ammonia/hydrochloric acid. The N-[4-(β-<2-methoxy-5-chlorobenzamido>-ethyl)-benzenesulfonyl]-N'-(3-methoxy-4-methylcyclohexyl)-urea which precipitates in crystalline form melts at 179° – 181°C after recrystallization from methanol.

EXAMPLE 6

N-[4-(β-<2-methoxy-5-chlorobenzamido>]-N'-(3-methoxy-4-methylcyclohexyl)-urea 8.2 g of N-[4-(β-acetamidoethyl)-benzenesulfonyl]-N'-(3-methoxy-4-methylcyclohexyl)-urea (melting point 151°–153°C) are heated under reflux for 2 hours with a solution of 1.6 g of sodium hydroxide in 30 ml of water. Then the whole is cooled at room temperature, 20 ml of acetone are added and 1.2 g of glacial acetic acid, and 4.1 g of 2-methoxy-5-chlorobenzoyl-chloride are added in portions. After stirring for 2 hours at room temperature the whole is filtered off with suction, the precipitate is treated with a solution of bicarbonate and then it is precipitated from dilute ammonia/hydrochloride acid. The N-[4-(β-<2-methoxy-5-chlorobenzamido>-ethyl)-benzenesulfonyl]-N'-(3-methoxy-4-methyl-cyclohexyl)-urea melts at 179° – 180°C after recrystallization from methanol/dimethylformamide.

EXAMPLE 7

N-[4-(β-<2-methoxy-5-chlorobenzamido>-ethyl)-benzenesulfonyl]-N'-(4-chlorocyclohexyl)-urea 8.5 g of N-[4-(β-<2-methoxy-5-chlorobenzamido>-ethyl)-benzene-sulfonyl]-methylurethane (melting point 189° – 191°C) are suspended in 100 ml of dioxane and 2.8 g of 4-chlorocyclohexylamine (boiling point at 82° – 84° C under a pressure of 7 mm of mercury, obtained by reaction of 4-aminocyclohexanol with phosphoruspentachloride) are added. The reaction mixture is heated to 110° C for 1 hour, the methanol formed during the reaction is distilling off, after cooling, water is added, which lead to the precipitation of the N-[4-(β-<2-methoxy-5-chlorobenzamido>-ethyl)-benzenesulfonyl]-N'-(4-chlorocyclohexyl)-urea which had formed. After recrystallization from methanol/dimethylformamide it melts at 177° – 178° C.

In analogous manner there is obtained: N-[4-(β-<2-methoxy-5-chlorobenzamido>-ethyl)-benzenesulfonyl]-N'-(2-chlorocyclohexyl)-urea, melting point 194° – 195°C (from methanol/dimethylformamide); from N-[4-(β-<3-chlorobenzamido>-ethyl)-benzenesulfonyl]-methylurethane (melting point 173° – 175° C):

N-[4-(β-<3-chlorobenzamido>-ethyl)-benzenesulfonyl]-N'-(2-chlorocyclohexyl)-urea, melting point 179° – 180° C (from methanol); from N-[4-(β-<2-methoxybenzamido>-ethyl)-benzenesulfonyl]-methylurethane (melting point 174° – 176° C):

N-[4-(β-<2-methoxybenzamido>-ethyl)-benzenesulfonyl]-N'-(4-chlorocyclohexyl)-urea, melting point 157° – 158°C (from methanol);

N-[4-(β-<2-methoxybenzamido>-ethyl)-benzenesulfonyl]-N'-(2-chlorocyclohexyl)-urea, melting point 198° – 199° C (from methanol/dimethylformamide); from N-[4-(β-<2-n-propoxybenzamido>-ethyl)-benzenesulfonyl]-methylurethane (melting point 159° – 161° C):

N-[4-(β-<2-n-propoxybenzamido>-ethyl)-benzenesulfonyl]-N'-(2-chlorocyclohexyl)-urea, melting point 100°– 102°C (from methanol);

N-[4-(β-<2-n-butoxybenzamido>-ethyl)-benzenesulfonyl]-methylurethane (melting point 160° – 162°C);

N-[4-β-<2-n-butoxybenzamido>-ethyl)-benzenesulfonyl]-N'-(2-chlorocyclohexyl)-urea, melting point 131° – 133° C (from methanol); from N-[4-(β-<2-methoxy-4-chlorobenzamido>-ethyl)-benzenesulfonyl]-methylurethane (melting point 178° – 180°C):

N-[4-(β-<2-methoxy-4-chlorobenzamido>-ethyl)-benzenesulfonyl]-N'-(4-chlorocyclohexyl)-urea, melting point 181°–182° C (from methanol); from N-[4-(β-<2-ethoxy-5-chlorobenzamido>-ethyl)-benzenesulfonyl]-methylurethane (melting point 203° – 205°C);

N-[4-(β-<2-ethoxy-5-chlorobenzamido>-ethyl)-benzenesulfonyl]N'-(3-methyl-Δ2-cyclopentenyl)-urea, melting point 138,5°-140,5° C;

N-[4-(β-<2-ethoxy-5-chlorobenzamido>-ethyl)-benzenesulfonyl]-N'-(2-chlorocyclohexyl)-urea, melting point 162° –164° C (from methanol); from N-[4-(β<2-methoxy-5-bromobenzamido>-ethyl)-benzenesulfonyl]-methylurethane (melting point 197° – 199°C)

N-[4-(β-<2-methoxy-5-bromobenzamido>-ethyl)-benzenesulfonyl]N'-(4-chlorocyclohexyl)-urea, melting point 180° – 182°C (from methanol) and N-[4-(β-<2-methoxy-5-bromobenzamido>-ethyl)-benzenesulfonyl]-N'-(2-chlorocyclohexyl)-urea, melting point 198° – 199°C (from methanol/dimethylformamide); from N-[4-(β-<2-ethoxy-5-fluorobenzamido>-ethyl)-benzenesulfonyl]-methylurethane (melting point 193° – 195°C)

N-[4-(β-<2-ethoxy-5-fluorobenzamido>-ethyl)-benzenesulfonyl]-N'-(4-chlorocyclohexyl)-urea, melting point 159° – 161°C (from methanol/dimethylformamide); from N-[4-(β-<2-methoxy-5-methylbenzamido>-ethyl)-benzenesulfonyl]-methylurethane (melting point 175° – 177°C)

N-[4-(β->2-methoxy-5-methylbenzamido>-ethyl)-benzenesulfonyl]-N'-(4-chlorocyclohexyl)-urea, melting point 110° – 112°C (from methanol) and N-[4-(β-<2-methoxy-5-methylbenzamido>-ethyl)-benzenesulfonyl]-N'-(2-chlorocyclohexyl)-urea, melting point 206° – 207°C (from methanol/dimethylformamide); from N-[4-(β-<2.5-dimethoxybenzamido>-ethyl)-benzenesulfonyl]-methylurethane (melting point 173°– 175°C)

N-[4-(β<2.5-dimethoxybenzamido>-ethyl)-benzenesulfonyl]-N'-(2-chlorocyclohexyl)-urea, melting point 143° – 145°C (from methanol); from N-[4-(β-<3.5-dimethylbenzamido>-ethyl)-benzenesulfonyl]-methylurethane (melting point 223° – 225°C)

N-[4-(β-<3.5-dimethylbenzamido>-ethyl)-benzenesulfonyl]-N'-(4-chlorocyclohexyl)-urea, melting point 179° – 181°C (from methanol) and N-[4-(β-<3.5-dimethylbenzamido>-ethyl)-benzenesulfonyl]-N'-(2-chlorocyclohexyl)-urea, melting point 202° – 204°C (from methanol); from N-[4-(β-<2-phenoxybenzamido>-ethyl)-benzenesulfonyl]-methylurethane (melting point 167° – 169°C)

N-[4-(β-<2-phenoxybenzamido>-ethyl)-benzenesulfonyl]-N'-(2-chloro-cyclohexyl)-urea, melting point 147° – 149°C (from methanol); from N-[4-(β-<3-methoxythiophen-2-carbonamido>-ethyl)-benzenesulfonyl]-methylurethane (melting point 226° –    °C)

N-[4-(β-<3-methoxythiophen-2-carbonamido>ethyl)-benzenesulfonyl]-N'-(2-chlorocyclohexyl)-urea, melting point 200°- 201°C (from methanol); from N -[4-(β-benzamido-ethyl)-benzenesulfonyl]-methylurethane (melting point 185° – 187°C)

N-[4-(β-benzamido-ethyl)-benzenesulfonyl]-N'-(2-chlorocyclohexyl)-urea, melting point 186° – 187°C (from methanol); from N-[4-β-<3-methylbenzamido>-ethyl)-benzenesulfonyl]-methylurethane (melting point 200° – 202°C)

N-[4-(β-<3-methylbenzamido>-ethyl)-benzenesulfonyl]-N'-(2-chlorocyclohexyl)-urea, melting point 179° – 181°C (from methanol); from N-[4-(β-<3-trifluoromethylbenzamido>-ethyl)-benzenesulfonyl]-methylurethane (melting point 178° – 180°C)

N-[4-(β-<3-trifluoromethylbenzamido>ethyl)-benzenesulfonyl]-N'-(2-chlorocyclohexyl)-urea, melting point 177° – 179°C (from methanol); from N-[4-(β-<3-chlorobenzamido>-ethyl)-benzenesulfonyl]-methylurethane (melting point 173° – 175°C)

N-[4-(β-<3-chlorobenzamido>-ethyl)-benzenesulfonyl]-N'-(4-chlorocyclohexyl)-urea, melting point 173° – 175°C (from methanol); from N-[4-(β-<3-methoxythiophen-2-carbonamido>-ethyl)-benzenesulfonyl]-methylurethane (melting point 226° – 228°C)

N-[4-(β-<3-methoxythiophen-2-carbonamido<ethyl)-benzenesulfonyl]-N'-(4-chlorocyclohexyl)-urea, melting point 196° – 197°C (from methanol/dimethylformamide); from N-[4-(β-<2-methoxy-5-chlorobenzamido>-ethyl)-benzenesulfonyl]-methylurethane (melting point 189° – 191°C)

N-[4-(β-<2-methoxy-5-chlorobenzamido>-ethyl)-benzenesulfonyl]-N'-(3-chlorocyclohexyl)-urea, melting point 144° – 146°C (from methanol/dimethylformamide); from
N-[4-(γ-<2-methoxy-5-chlorobenzamido>-propyl)-benzenesulfonyl]-methylurethane (melting point 160°C)
N-[4-(γ-<2-methoxy-5-chlorobenzamido>-propyl)-benzenesulfonyl]-N'-(2-chlorocyclohexyl)-urea, melting point 93° (decomposition) (from methanol/water); from
N-[4-(β-<2-methoxy-5-chlorobenzamido>-propyl)-benzenesulfonyl]-methylurethane (melting point 197°C)
N-[4-(β-<2-methoxy-5-chlorobenzamido>-propyl)-benzenesulfonyl]-N'-(2-chlorocyclohexyl)-urea, melting point 78°C (decomposition) (from methanol/water); from
N-[4-(β-<3-chlorobenzamido>-ethyl)-benzenesulfonyl]-methylurethane (melting point 173°–175°C)
N-[4-(β-<3-chlorobenzamido -ethyl)-benzenesulfonyl]-N'-(3-chloro-cyclohexyl)-urea, melting point 151° – 153°C (from methanol); from
N-[4-(β-<2-methoxy-5-methylbenzamido>-ethyl)-benzenesulfonyl]-methylurethane (melting point 175° – 177°C)
N-[4-(β-<2-methoxy-5-methylbenzamido>-ethyl)-benzenesulfonyl]-N'-(3-chlorocyclohexyl)-urea, melting point 146° – 148°C (from methanol); from
N-[4-<3-ethoxythiophen-2-carbonamido>-benzenesulfonyl]-methylurethane (melting point 163°-165°C)
N-[4-(β-<3-ethoxythiophen-2-carbonamido>-ethyl)-benzenesulfonyl]-N'-(2-chlorocyclohexyl)-urea, melting point 176°–177°C (from methanol); from
N-[4-β-<2-allyloxy-5-chlorobenzamido>-ethyl)-benzenesulfonyl]-methylurethane (melting point 167°–169°C)
N-[4-(β-<2-allyloxy-5-chlorobenzamido>-ethyl)-benzenesulfonyl]-N'-(2-chlorocyclohexyl)-urea, melting point 145°–147°C (from methanol);

EXAMPLE 8

N-[4-(β-<2-methoxy-5-chlorobenzamido>-ethyl)-benzenesulfonyl]-N'-(4-chlorocyclohexyl)-urea 4.26 g of N-[4-(β-<2-methoxy-5-chlorobenzamido>-ethyl)-benzenesulfonyl-methyl-urethane are heated for 1 ½ hours in a reflux condenser in 100 ml dioxane with 2 g of 4-chlorocyclohexylamine-acetate. After addition of water and recrystallization of the precipitating product from methanol/dimethylformamide there is obtained in good yield the N-[4-<2-methoxy-5-chlorobenzamido>-ethyl)-benzenesulfonyl]-N'-(4-chlorocyclohexyl)-urea melting at 177°–178°C.

EXAMPLE 9

N-[4-(β-<2-methoxy-5-chlorobenzamido>-ethyl)-benzenesulfonyl]-N'-(2-chlorocyclohexyl)-urea A mixture of 10.3 g of of N-[4-<2-methoxy-5-chlorobenzamido>-ethyl)-benzenesulfonyl]-ethyl)-benzenesulfonyl-urea (melting point 171°–173°C), 300 ml of toluene, 30 ml of glycolmonomethyl-ether, 1.65 g of glacial acetic acid and 3.3 g of 2-chloro-cyclohexylamine are heated under reflux for 5 hours. Then the whole is concentrated in vacuo and the residue is treated with alcohol. The N-[4-(β<2-methoxy-5-chlorobenzamido>-ethyl)-benzenesulfonyl]-N'-(2-chlorocyclohexyl)-urea obtained as crude product melts at 194°–195°C after recrystallization from methanol/dimethylformamide.

EXAMPLE 10

N-[4-(β-<2-methoxy-5-chlorobenzamido>-ethyl)-benzenesulfonyl]-N'-(4-chlorocyclohexyl)-urea 3.9 g of 4-(β-<2-methoxy-5-chlorobenzamido>-ethyl)-benzenesulfonamide sodium, 6.5 g of N.N-diphenyl-N'-(4-chlorocyclohexyl)-urea (melting point 115°–116°C) and 100 ml dimethyl formamide are heated to 110°C for 45 minutes. Then the whole is cooled, poured into water and ammonia of 1 % strength is added. Then the whole is filtered, the filtrate is acidified and the precipitate obtained is purified once more over ammonia/hydrochloric acid. The N-[4-(β-<2-methoxy-5-chlorobenzamido>-ethyl)-benzenesulfonyl]-N'-(4-chlorocyclohexyl)-urea precipitating in crystalline form melts at 178°–179°C after recrystallization from methanol/dimethylformamide.

EXAMPLE 11

N-[4-(β->2-methoxy-5-chlorobenzamido>-benzenesulfonyl]-N'-(4-chlorocyclohexyl)-urea 7.8 g of N-[4-(β-acetoamido-ethyl)-benzenesulfonyl]-N'-(4-chlorocyclohexyl)-urea (melting point 151°–153°C) are heated under reflux for 2 hours with 1.6 g of sodium hydroxide and 30 ml of water. Then the whole is cooled to room temperature, 20 ml of acetone are added and 1.2 g of glacial acetic -chlorobenzamido>-ethyl)-benzenesulfonyl] acid, and 4.1 g of 2-methoxy-5-chlorobenzoylchloride are added in portions and stirring is continued for 1 hour. The precipitate if filtered off with suction, stirred with bicarbonate solution and recrystallized from methanol/dimethylformamide. The N-[4-(β-<-methoxy-5-chlorobenzamido>-ethyl)-benzenesulfonyl]-N'-(4-chlorocyclohexyl)-urea obtained melts at 178°–179°C.

EXAMPLE 12

N-[4-(β-<2-methoxy-4-chlorobenzamide]-ethyl)-benzenesulonyl]-N'-(2-chlorocyclohexyl)-urea 5 g of 4-(β-<2-methoxy-4-chlorobenzamido>-ethyl)-benzenesulfonamide (melting point 185° – 186°C) are dissolved in 7 ml of 2N sodium hydroxide solution and 50 ml of acetone and 2.3 g of 2-chlorocyclohexyl-isocyanate are added dropwise while stirring at 0° – 5°C. Then stirring is continued for 2 hours, the whole is diluted with water and methanol, and any undissolved matter is filtered off and the filtrate is acidified with hydrochloric acid. The N-[4-(β-<2-methoxy-4-chlorobenzamido>-ethyl)-benzenesulfonyl]-N'-(2-chlorocyclohexyl)-urea precipitating, melts at 174° – 176°C after recrystallization from methanol.

In analogous manner there is obtained: from
4-(β-<4-chlorobenzamido>-ethyl)-benzenesulfonamide (melting point 225° – 226°C)
N-[4-(β-<4-chlorobenzamido>-ethyl)-benzenesulfonyl]-N'-(2-chlorocyclohexyl)-urea, melting point 180° – 181°C (from methanol); from
4-(β-<2-ethoxybenzamido>-ethyl)-benzenesulfonamide (melting point 148° – 150°C)

N-[4-(β-<2-ethoxybenzamide>-ethyl)-benzenesulfonyl]-N'-(2-chlorocyclohexyl)-urea, melting point 147° – 148°C (from methanol); from 4-(β-<3.5-dimethylthiophen-2-carbonamido>-ethyl)-benzenesulfonamide (melting point 176° – 177°C)

N-[4-(β-<3.5-dimethylthiophen-2-carbonamido>-ethyl)-benzenesulfonyl]-N'-(2-chlorocyclohexyl)-urea, melting point 177° – 179°C (from methanol);

EXAMPLE 13

N-[4-(β-<2-methoxy-5-chlorobenzamido>-ethyl)-benzenesulfonyl]-N'-(4-chlorocyclohexyl)-urea a. 2.3 g of 4-chlorocyclohexyl-parabanic acid (melting point 222° – 223°C) are suspended in 50 ml benzene and heated under reflux for 2 hours with 3.9 g of 4-(β-<2-methoxy-5-chlorobenzamido>-ethyl)-benzenesulfochloride and 1 g of triethylamine. The solvent is decanted, the remaining oil is treated with water and the undissolvable residue is recrystallized from methanol. The 1-[4-(β-<2-methoxy-5-chlorobenzamido>-ethyl-)-benzenesulfonyl]-3-(4-chlorocyclohexyl)-parabanic acid melts at 179° – 181°C.

b. 0.9 g of the above-mentioned compound is heated in a vapor bath for 45 minutes in 5 ml of dioxane and 10 ml of 1N sodium hydroxide solution. Then water is added, acidified and recrystallized from methanol. There is obtained the N-[4-(β-<2-methoxy-5-chlorobenzamido>-ethyl)-benzenesulfonyl]-N'-(4-chlorocyclohexyl)-urea melting at 179° – 181°C.

EXAMPLE 14

N-[4-(β-<2-methoxy-5-chlorobenzamido>-ethyl)-benzenesulfonyl]-N'-2-chlorocyclohexyl urea a. 1 g of N-[4-(β-<2-methoxy-4-chlorobenzamido>-ethyl)-benzenesulfonyl-N'-2-chlorocyclohexyl-thiourea (melting point 173° – 175°C) is dissolved in 100 ml of methanol to which 10 ml of dioxane are added. 1.1 g of mercury peroxide are added and stirring is continued for 3 hours at 50° – 60°C. After filtration from the mercury sulfide, the whole is concentrated in vacuo. The N-[4-(β-<2-methoxy-5-chlorobenzamido>-ethyl)-benzenesulfonyl-N'-2-chlorocyclohexyl-isourea methyl ether melts at 125° – 127°C after recrystallization from dilute methanol.

b. 0.1 g of the product obtained according to (a) is suspended in 2 ml dioxane and 10 ml concentrated hydrochloric acid. Then the whole is heated for 5 minutes in a vapor bath, water is added and the precipitate is filtered off with suction and crystallized from methanol. The N-[4-(β-<2-methoxy-5-chlorobenzamido>-ethyl)-benzenesulfonyl]-N'-2-chlorocyclohexyl-urea melts at 192° – 194°C.

EXAMPLE 15

N-[4-(β-<2-methoxy-5-chlorobenzamido>-ethyl)-benzenesulfonyl]-N'-2-chlorocyclohexyl-urea 0.5 of N-[4-9β<2-methoxy-5-chlorobenzamido>-ethyl)-benzenesulfonyl]-N'-2-chlorocyclohexyl-thiourea (melting point 173° – 175°C) is dissolved in 30 ml 2N sodium hydroxide solution, and 10 ml of hydrogen peroxide of 30 % strength are added.

Then the whole is heated for 20 minutes in a vapor bath, cooled and acidified. A precipitate is obtained which is filtered off with suction, and treated with highly diluted ammonia. After filtration it is acidified. The N-[4-(β-<2-methoxy-5-chlorobenzamido>-ethyl)-benzenesulfonyl]-N'-2-chlorocyclohexyl-urea melts at 192° – 194°C after recrystallization from methanol.

EXAMPLE 16

N-[4-(β-benzamido-ethyl)-benzenesulfonyl]-N'-(4-methyl-Δ3-cyclohexenyl)-urea 7.6 g of 4-(β-benzamido-ethyl)-benzenesulfonamide are heated for 3 hours in a reflux condenser while stirring in 150 ml of acetone with 5 g of potassium carbonate. Then 3.5 g of 4-methyl-Δ3-cyclohexenyl-isocyanate (boiling point of 72° – 74°C under a pressure of 12 mm of mercury prepared by decomposition of the 4-methyl-Δ3-cyclohexene carboxylic acid azide obtained in usual manner from 4-methyl-Δ3-cyclohexenecarboxylic acid) are added and stirring is continued for 8 hours at boiling temperature. The solvent is evaporated, and the residue is treated with water, filtered and the filtrate is acidified. The N-[4-(β-benzamido-ethyl)-benzenesulfonyl]-N'-(4-methyl-Δ3-cyclohexanyl)-urea filtered off with suction, is recrystallized from dilute ehtanol and melts at 195° – 196°C.

In analogous manner there is obtained: from
4-(β<2-methoxy-5-chloro-benzamido>-ethyl)-benzenesulfonamide (melting point 214° – 216°C)
N-[4-(β-<2-methoxy-5-chloro-benzamido>-ethyl)-benzenesulfonyl]-N'-(4-methyl-Δ3-cyclohexenyl)-urea, melting point 158° – 160°C; from
4-(β-<2-methoxy-benzamido>-ethyl)-benzenesulfonamide (melting point 178° – 180°C)
N-[4-(β-<2-methoxy-benzamido>-ethyl)-benzenesulfonyl]-N'-(4-methyl-Δ3 -cyclohexenyl)-urea, melting point 173° – 175°C; from
4-(β-<3-chlorobenzamido>-ethyl)-benzenesulfonamide (melting point 161° – 163°C)
N-[4-(β-<3-chlorobenzamido>-ethyl)-benzenesulfonyl]-N'-(4-methyl-Δ3-cyclohexenyl)-urea, melting point 147° – 149°C; from
4-(β-<4-chloro-benzamido>-ethyl)-benzenesulfonamide (melting point 220° – 221°C)
N-[4-(β-<4-chloro-benzamido>-ethyl)-benzenesulfonyl]-N'-(4-methyl-Δ3-cyclohexenyl)-urea, melting point 201° – 203°C; from
4-(β-<3-methyl-benzamido>-ethyl)-benzenesulfonamide (melting point 187° – 189°C)
N-[4-(β-<3-methyl-benzamido>-ethyl)-benzenesulfonyl]-N'-(4-methyl-Δ3-cyclohexenyl)-urea, melting point 160° – 162°C; from
4-(β-(β2-methoxy-4-chloro-benzamido>-ethyl)-benzenesulfonamide (melting point 187° – 188°C)
N-[4-9β-<2-methoxy-4-chloro-benzamido>-ethyl)-benzenesulfonyl]-N'-(4-methyl-Δ3-cyclohexenyl)-urea, melting point 160° – 162°C; from
4-(β-<2,4-dichloro-benzamido>-ethyl)-benzenesulfonamide (melting point 162° – 164°C)
N-[4-(β-<2,4-dichloro-benzamido>-ethyl)-benzenesulfonyl]-N'-(4-methyl-Δ3-cyclohexenyl)-urea, melting point 178° – 180°C; from
4-(β-<2-ethoxy-benzamido>-ethyl)-benzenesulfonamide (melting point 148° – 150°C) N-[4-(β-<2-ethoxy-benzamido>-ethyl)-benzenesulfonyl]-N'-(4-methyl-Δ3-cyclohexenyl)-urea, melting point 158° – 160°C; from
4-(β-<2-isoamyloxy-benzamido>-ethyl)-benzenesulfonamide (melting point 148°C)

N-[4-(β-<2-isoamyloxy-benzamido>-ethyl)-benzenesulfonyl]-N'-(4-methyl-Δ3-cyclohexenyl)-urea, melting point 140° – 142°C; from
4-(β-<2-allyloxy-benzamido>-ethyl)-benzenesulfonamide (melting point 129° – 130°C)
N-[4-(β-<2-allyloxy-benzamido>-ethyl)-benzenesulfonyl]-N'-(4-methyl-Δ3-cyclohexenyl)-urea, melting point 144° – 146°C; from
4-(β-<2-isoamyloxy-5-chloro-benzamido>-ethyl)-benzenesulfonamide (melting point 142° – 144°C)
N-[4-(β-<2-isoamyloxy-5-chloro-benzamido>-ethyl)-benzenesulfonyl]-N'-(4-methyl-Δ3-cyclohexenyl)-urea, melting point 124° – 126°C; from
4-(β-<3-fluoro-benzamido>-ethyl)-benzenesulfonamide (melting point 218° – 219°C)
N-[4-(β-<3-fluoro-benzamido>-ethyl)-benzenesulfonyl]-N'-(4-methyl-Δ3-cyclohexenyl)-urea, melting point 188° – 190°C; from
4-(β-<3-chloro-4-methyl-benzamido>-ethyl)-benzenesulfonamide (melting point 184° – 185°C)
N-[4-(β-<3-chloro-4-methyl-benzamido>-ethyl)-benzenesulfonyl]-N'-(4-methyl-Δ3-cyclohexenyl)-urea, melting point 185° – 187°C; from
4-(β-<2,5-dimethyl-benzamido>-ethyl)-benzenesulfonamide (melting point 139° – 141°C)
N-[4-(β-<2,5-dimethyl-benzamido>-ethyl)-benzenesulfonyl]-N'-(4-methyl-Δ3-cyclohexenyl)-urea, melting point 173° – 175°C from
4-(β-<naphthalene-2-carbonamido>-ethyl)-benzenesulfonamide (melting point 206° – 208°C)
N-[4-(β-<naphthalene-2-carbonamido>-ethyl-benzenesulfonyl]-N'-(4-methyl-Δ3-cyclohexenyl)-urea, melting point 180° – 182°C; from
4-(β-<4-nitro-benzamido>-ethyl)-benzenesulfonamide (melting point 182° – 184°C)
N-[4-(β-<4-nitro-benzamido>-ethyl)-benzenesulfonyl]-N'-(4-methyl-Δ3-cyclohexenyl)-urea, melting point 172° – 174°C; from
4-(β-<2-methoxy-5-methyl-benzamido>-ethyl)-benzenesulfonamide (melting point 193° – 194°C)
N-[4-(β-<2-methoxy-5-methyl-benzamido>-ethyl)-benzenesulfonyl]-N'-(4-methyl-Δ3-cyclohexenyl)-urea, melting point 149° – 151°C; from
4-(β-<2-ethoxy-5-methyl-benzamido>-ethyl)-benzenesulfonamide (melting point 151° – 153°C)
N-[4-(β-<2-ethoxy-5-methyl-benzamido>-ethyl)-benzenesulfonyl]-N'-(4-methyl-Δ3-cyclohexenyl)-urea, melting point 158° – 159°C.

EXAMPLE 17

N-[4-(β-<2-methoxy-4-chloro-benzamido>-ethyl)-benzenesulfonyl]-N'-(4-methyl-Δ3-cyclohexenyl)-urea 4.2 g of N-[4-(β-<2-methoxy-4-chloro-benzamido>ethyl)-benzenesulfonyl]-methyl-urethane (melting point 178° – 180°C) are heated to 110°C while stirring, in 50 ml dioxane with 4-methyl-Δ3-cyclohexenylamine (boiling point at 50°C under a pressure of 10 mm of mercury, prepared from 4-methyl-Δ3-cyclohexenyl-isocyanate by saponification with acetic acid of 50 % strength); during this process methanol which has formed is distilled off. Then dioxane is evaporated to a large extent under reduced pressure and water is added to the residue. The product which has precipitated is filtered off with suction and recrystallized from dilute ethanol. The N-[4-(β-<2-methoxy-4-chloro-benzamido>-ethyl)-benezenesulfonyl]-N'-(4-methyl-Δ3-cyclohexenyl)-urea melts at 160° – 162°C.

EXAMPLE 18

N-[4-(β-<2-methoxy-5-chlorobenzamido>-ethyl-benzenesulfonyl]-N'-(3.4-dimethylcyclohexyl)-urea 5.7 g of N-[4-(β-<2-methoxy-5-chlorobenzamido>-ethyl)-benzenesulfonyl]-methyl-urethane (melting point 189° – 191°C) are suspended in 100 ml dioxane and 1.7 g of 3.4-dimethylcyclohexylamine (boiling point at 47°C under a pressure of 6 mm of mercury, acetate: melting point 114° – 115°C) are added. Then the whole is heated to 110°C for 1½ hours while stirring, and the methanol which has formed during the reaction is distilled off. When adding a small amount of water the N-[4-(β-<2-methoxy-5-chlorobenzamido>-ethyl)-benzenesulfonyl]-N'-(3.4-dimethylcyclohexyl)-urea crystallizes and melts after recrystallization from methanol at 170° – 171°C.

In analogous manner there is obtained:
N-[4-(β-<2-methoxy-5-chlorobenzamido>-ethyl)-benzenesulfonyl]-N'-(4.4-dimethylcyclohexyl)-urea, melting point 177° – 178°C (from methanol)
N-[4-(β-<2-methoxy-5-chlorobenzamido>-ethyl)-benzenesulfonyl]-N'-(3.5-dimethylcyclohexyl)-urea, melting point 193°C (from methanol/dimethylformamide) and
N-[4-(β-<2-methoxy-5-chlorobenzamido>-ethyl)-benzenesulfonyl]-N'-(4.4-diethylcyclohexyl)-urea, melting point 174° – 175°C (from methanol); from
N-[4-(β-<2-ethoxy-5-chlorobenzamido>-ethyl)-benzenesulfonyl]-methylmethane (melting point 203° – 204°C)
N-[4-(β-<2-ethoxy-5-chlorobenzamido>-ethyl)-benzenesulfonyl]-N'-(4.4-diethylcyclohexyl)-urea, melting point 136° – 138°C (from methanol); from
N-[4-(β-<2-allyloxy-5-chlorobenzamido>-ethyl)-benzenesulfonyl]-methylurethane (melting point 167° – 168°C)
N-[4-(β-<2-allyloxy-5-chlorobenzamido>-ethyl)-benzenesulfonyl]-N'-(3.4-dimethylcyclohexyl)-urea, melting point 158° – 160°C (from methanol) and
N-[4-(β-<2-allyloxy-5-chlorobenzamido>-ethyl)-benzenesulfonyl]-N'-(4.4-dimethylcyclohexyl)-urea, melting point 156° – 158°C (from methanol); from
N-[4-(β-<2-methoxy-5-fluorobenzamido>-ethyl)-benzenesulfonyl]-methylurethane (melting point 171° – 173°C)
N-[4-(β-<2-methoxy-5-fluorobenzamido>-ethyl)-benzenesulfonyl]-N'-(2.4-dimethylcyclohexyl)-urea, melting point 175° – 176°C (from methanol)
N-[4-(β-<2-methoxy-5-fluorobenzamido>-ethyl)-benzenesulfonyl]-N'-(3.4-dimethylcyclohexyl)-urea, melting point 180° – 182°C (from methanol)
N-[4-(β-<2-methoxy-5-fluorobenzamido>-ethyl)-benzenesulfonyl]-N'-(4.4-dimethylcyclohexyl)-urea, melting point 196° – 197°C (from methanol); from
N-[4-(β-<2-ethoxy-5-fluorobenzamido>-ethyl)-benzenesulfonyl]-methylurethane (melting point 193° – 195°C)
N-[4-(β-<2-ethoxy-5-fluorobenzamido>-ethyl)-benzenesulfonyl]-N'-(4.4-dimethylcyclohexyl)-urea, melting point 167° – 168°C; from N-[4-(β-<2-methoxy-5-bromobenzamido>-ethyl)-benzenesulfonyl]-methylurethane (melting point 197° – 199°C)

N-[4-(β-<2-methoxy-5-bromobenzamido>-ethyl)-benzenesulfonyl]-N'-(2.4-dimethylcylohexyl)-urea, melting point 204° – 205°C (from methanol/dimethylformamide)

N-[4-(β-<2-methoxy-5-bromobenzamido>-ethyl)-benzenesulfonyl]-N-(3.4-dimethylcyclohexyl)-urea, melting point 166° – 168°C (from methanol) and N-[4-(β-<2-methoxy-5-bromobenzamido>-ethyl)-benzenesulfonyl]-N'-(3.5-dimethylcyclohexyl)-urea, melting point 202° – 204°C (from methanol/dimethylformamide); from N-[4-(β-<2-methoxy-5-methylbenzamido>-ethyl)-benzenesulfonyl]-methylurethane (melting point 175° – 177°C)

N-[4-(β-<2-methoxy-5-methylbenzamido>-ethyl)-benzenesulfonyl]-N'-(4.4-dimethylcyclohexyl)-urea, melting point 164° – 166°C (from methanol; from N-[4-(β-<2.5-dimethoxybenzamido>-ethyl)-benzenesulfonyl]-methylurethane (melting point 173° – 175°C)

N-[4-(β-<2.5-dimethoxybenzamido>-ethyl)-benzensulfonyl]-N'-(3.4-dimethylcyclohexyl)-urea, melting point 157° – 159°C (from methanol)

N-[4-(β-<2.5-dimethoxybenzamido>-ethyl-benzenesulfonyl]-N'-(4.4-dimethylcyclohexyl)-urea, melting point 132° – 134°C (from methanol) and N-[4-(β-<2.5-dimethoxybenzamido>-ethyl)-benzenesulfonyl]-N'-(4.4-diethylcyclohexyl)-urea, melting point 142° – 144°C (from methanol); from N-[4-(β-<2-ethoxy-5-acetylbenzamido>-ethyl)-benzenesulfonyl]-methylurethane (melting point 164° – 166°C)

N-[4-(β-<2-ethoxy-5-acetylbenzamido>-ethyl)-benzenesulfonyl]-N'-(4.4-dimethylcyclohexyl)-urea, melting point 138° – 140°C (from methanol); from N-[4-(β-<2-methoxybenzamido>-ethyl)-benzenesulfonyl]-methylurethane (melting point 174° – 176°C)

N-[4-(β-<2-methoxybenzamido>-ethyl)-benzenesulfonyl]-N'-(2.4-dimethylcyclohexyl)-urea, melting point 197° – 199°C (from methanol/dimethylformamide)

N-[4-(β-<2-methoxybenzamido>-ethyl)-benzenesulfonyl]-N'-(3.4-dimethylcyclohexyl)-urea, melting point 169° – 171°C (from methanol)

N-[4-(β-<2-methoxybenzamido>-ethyl)-benzenesulfonyl]-N'-(3.5-dimethylcyclohexyl)-urea, melting point 179° – 181°C (from methanol) and N-[4-(β-<2-methoxybenzamido>-ethyl)-benzenesulfonyl]-N'-(4.4-dimethylcyclohexyl)-urea, melting point 188° – 189°C (from methanol/dimethylformamide); from N-[4-(β-<2-propoxybenzamido>-ethyl)-benzenesulfonyl]-methylurethane (melting point 159° – 161°C) N-[4-(β-<2-propoxybenzamido>-ethyl)-benzenesulfonyl]-N'-(4.4-dimethylcyclohexyl)-urea, melting point 183° – 184°C (from methanol); from N-[4-(β-<3-methylbenzamido>-ethyl)-benzenesulfonyl]-methylurethane (melting point 200° – 202°C)

N-[4-(β-<3-methylbenzamido>-ethyl)-benzenesulfonyl]-N'-(4.4-dimethylcyclohexyl)-urea, melting point 170° – 172°C (from methanol); from N-[4-(β-<3-chlorobenzamido>-ethyl)-benzenesulfonyl]-methylurethane (melting point 173° – 175°C)

N-[4-(β-<3-chlorobenzamido>-ethyl)-benzenesulfonyl]-N'-(3.4-dimethylcyclohexyl)-urea, melting point 163° – 165°C (from methanol)

N-[4-(β-<3-chlorobenzamido>-ethyl)-benzenesulfonyl]-N'-(4.4-dimethylcyclohexyl)-urea, melting point 168° – 169°C (from methanol) and N-[4-(β-<3-chlorobenzamido>-ethyl)-benzenesulfonyl]-N'-(4.4-diethylcyclohexyl)-urea, melting point 175° – 176°C (from methanol); from N-[4-(β-<3.5-dimethylbenzamido>-ethyl)-benzenesulfonyl]-methylurethane (melting point 223° – 225°C)

N-[4-(β-<3.5-dimethylbenzamido>-ethyl)-benzenesulfonyl]-N'-(4.4-dimethylcyclohexyl)-urea, melting point 194° – 195°C (from methanol); from N-[4-(β-<3-ethoxythiophen-2-carbonamido>-ethyl)-benzenesulfonyl]-methylurethane (melting point 163° – 165°C)

N[4-(β-<3-ethoxythiophen-2-carbonamido>-ethyl)-benzenesulfonyl]-N'-(4.4-dimethylcyclohexyl)-urea, melting point 181° – 183°C (from methanol); from N-[4-(β-<3.4-tetramethylenethiophen-2-carbonamido>-ethyl)-benzenesulfonyl]-methylurethane (melting point 194° – 196°C)

N-[4-(β-<3.4-tetramethylenethiophen-2-carbonamido>-ethyl)-benzenesulfonyl]-N'-(4.4-dimethylcyclohexyl)-urea, melting point 186° – 187°C (from methanol).

EXAMPLE 19

N-[4-(β-<2-methoxy-benzamido>-ethyl)-benzenesulfonyl-N'-(4.4-diethyl-cyclohexyl)-urea 6 g of 4-(β-<2-methoxybenzamido>-ethyl)-benzenesulfonamide (melting point 178° – 180°C) are dissolved in 9 ml of 2N sodium hydroxide solution and 40 ml of acetone and 3.3 g of 4.4-diethyl-cyclohexyl-isocyanate (boiling point at 108° – 110°C under a pressure of 11 mm of mercury; obtained by reaction of 4.4-diethyl-cyclohexylamine (boiling point at 95° – 97°C, hydrochloride: boiling point 243°C) with phosgene) are added dropwise while stirring at 0° – 5°C. Stirring is continued for 2 – 3 hours at room temperature, the whole is diluted with water and methanol, then the whole is filtered from the undissolved matter and the filtrate is acidified with dilute hydrochloric acid. The N-[4-(β-<2-methoxy-benzamido>-ethyl)-benzenesulfonyl]-N'-(4.4-diethyl-cyclohexyl)-urea precipitating in crystalline form melts after recrystallization from methanol at 186° – 187°C.

In analogous manner there is obtained: from
4-(β-<2-n-butoxybenzamido>-ethyl)-benzenesulfonamide (melting point 151°–152°C)

N-[4-(β-<2-n-butoxybenzamido>-ethyl)-benzenesulfonyl]-N'-(2.4-dimethylcyclohexyl)-urea, melting point 190°–191°C (from methanol/dimethylformamide); from 4-(β-<2-methoxy-5-methylbenzamido>-ethyl)-benzenesulfonamide (melting point 197°–198°C)

N-[4-(β-<2-methoxy-5-methylbenzamido>-ethyl)-benzenesulfonyl]-N'-(2.4-dimethylcyclohexyl)- urea, melting point 191°–192°C (from methanol/-dimethylformamide) and

N-[4-(β-<2-methoxy-5-methylbenzamido>-ethyl)-benzenesulfonyl]-N'-(3.5-dimethylcyclohexyl)-urea, melting point 203°–204°C (from methanol/dimethylformamide); from 4-(β-<2-methoxy-4-chlorobenzamido>-ethyl)-benzenesulfonamide (melting point 187°–188°)

N-[4-(β-<2-methoxy-4-chlorobenzamido>-ethyl)-benzenesulfonyl]-N'-(2.4-dimethylcyclohexyl)-urea, melting point 186°–188°C (from methanol) and N-[4-(β-<2-methoxy-4-chlorobenzamido>ethyl)-benzenesulfonyl]-N'-(4.4-dimethylcyclohexyl)-urea, melting point 201°–203°C (from methanol); from 4-(β-<2-ethoxy-5-chlorobenzamido>ethyl)-benzenesulfonamide (melting point 168°–170°C)

N-[4-(β-<2-ethoxy-5-chlorobenzamido>ethyl)-benzenesulfonyl]-N'-(2.4-dimethylcyclohexyl)-urea, melting point 195°–196°C (from methanol); from 4-(β-<2-ethoxy-5-acetylbenzamido>-ethyl)-benzenesulfonamide (melting point 197°–198°C)

N-[4-(β-<2-ethoxy-5-acetylbenzamido>-ethyl)-benzenesulfonyl]-N'-(2.4-dimethylcyclohexyl)-urea, melting point 168°–169°C (from methanol); from 4-(β-<2-β-methoxyethoxybenezamido>-ethyl)-benzenesulfonamide (melting point 128°–130°C)

N-[4-(β-<2-β-methoxyethoxybenzamido>-ethyl)-benzenesulfonyl]-N'-(2.4-dimethylcyclohexyl)-urea, melting point 164°–165°C (from methanol) and N-[4-(β-<2-β-methoxyethoxybenzamido>-ethyl)-benzenesulfonyl]-N'-(4.4-dimethylcyclohexyl)-urea, melting point 190°–191°C (from methanol); from 4-(β->2-β-methoxy-ethoxy-5-chlorobenzamido>-ethyl)-benzenesulfonamide (melting point 161°–162°C)

N-[4-(β-<2-β-methoxy-ethoxy-5-chlorobenzamido>-ethyl)-benzenesulfonyl]-N'-(2.4-dimethylcyclohexyl)-urea, melting point 163°–164°C (from methanol); from 4-(2-methoxybenzamido-methyl)-benzenesulfonamide (melting point 190°–191°C)

N-[4-2-methoxybenzamido-methyl)-benzenesulfonyl]-N'-(4.4-dimethyl cyclohexyl)-urea, melting point 210°–211°C (from methanol); from 4-(β->2-phenoxybenzamido>-ethyl)-benzenesulfonamide (melting point 187°–188°C)

N-[4-(β-<2-phenoxybenzamido>-ethyl)-benzenesulfonyl]-N'-(2.4- dimethylcyclohexyl)-urea, melting point 167°–168°C (from methanol) and N-[4-(β-<2-phenoxybenzamido<-ethyl)-benzenesulfonyl]-N'-(4.4-dimethylcyclohexyl)-urea, melting point 148°–150°C (from methanol); from 4-(β-<3-methylbenzamido>-ethyl)-benzenesulfonamide (melting point 187°–189°C)

N-[4-(β-<3-methylbenzamido>-ethyl)-benzenesulfonyl]-N'-(2.4-dimethylcyclohexyl)-urea, melting point 178°–180°C (from methanol); from 4-(β-<N-methyl-3-methylbenzamido>-ethyl)-benzenesulfonamide (melting point 146°C)

N-[4-(β->N-methyl-3-methylbenzamido>-ethyl)-benzenesulfonyl ]-N'-(4.4-diethylcyclohexyl)-urea, melting point 141°–142°C (from methanol); from 4-(β-<3.5-dimethylbenzamido>-ethyl)-benzenesulfonamide (melting point 194°–196°C)

N-[4-(β-<3.5-dimethylbenzamido>-ethyl)-benzenesulfonyl]-N'-(2.4-dimethylcyclohexyl)-urea, melting point 202°–204°C (from methanol); from 4-(β-<3-trifluoromethylbenzamido>-ethyl)-benzenesulfonamide (melting point 145°–147°C)

N-[4-(β-<3-trifluoromethylbenzamido>-ethyl)-benzenesulfonyl]-N'-(2.4-dimethylcyclohexyl)-urea, melting point 185°–187°C (from methanol) and N-[4-(β-<3-trifluoromethylbenzamido>-ethyl)-benzensuflonyl]- N'-(4.4-dimethylcyclohexyl)-urea, melting point 169°–170°C (from methanol); from 4-(β-<3-methoxythiophen-2-carbonamido>-ethyl)-benzenesulfonamide (melting point 201°–203°C)

N-[4-(β-<3-methoxythiophen-2-carbonamido>-ethyl)-benzenesulfonyl]-N'-(2.4-dimethylcyclohexyl)-urea, melting point 175°–176°C (from methanol; from 4-(β-<3-ethoxythiophen-2-carbonamido>-ethyl)-benzenesulfonamide (melting point 177°–179°C)

N-[4-(β-<3-ethoxythiophen-2-carbonamido>-ethyl)-benzenesulfonyl]-N'-(2.4-dimethylcyclohexyl)-urea, melting point 168°–169°C (from methanol); from 4-(β-<3-benzyloxythiophen-2-carbonamido>-ethyl)-benzenesulfonamide (melting point 196°–198°C)

N-[4-(β-<3-benzyloxythiophen-2-carbonamido>-ethyl)-benzenesulfonyl]-N'-(4.4-dimethylcyclohexyl)-urea, melting point 181°–182°C (from methanol/dimethylformamide).

EXAMPLE 20

N-[4-(β-<2-methoxy-5-chlorobenzamido>-ethyl)-benzenesulfonyl]-N'-(2.4-dimethyl-cyclohexyl)-urea 8.2 g of N-[4-(β-<2-methoxy-5-chloro-benzamido>-ethyl)-benzenesulfonyl]-urea.(melting point 171°–173°C) are suspended in 150 ml of dioxane and heated under reflux for 1 hour after addition of 3.75 g of 2.4-dimethyl-cyclohexyl-amine-acetate. Then the solvent is distilled off in vacuo and water is added to the residue. The crystals obtained of N-[4-(β-<2-methoxy5-chlorobenzamido>-ethyl)-benzenesulfonyl]-N'-(2.4-dimethylcyclohexyl)-urea are recrystallized from methanol/dimethyl formamide and melt at 200°–201°C.

EXAMPLE 21

N-[4-(β-<2-methoxy-5-chlorobenzamido>-ethyl)-benzenesulfonyl]-N'-(4.4-dimethylcyclohexyl)-urea a. 5.6 g of 4.4-dimethylcyclohexyl parabanic acid (melting point 182°–183°C, prepared by reaction of 4.4-dimethylcyclohexyl-urea with oxalylchloride) are heated under reflux for 1½ hours together with 9.7 g of 4-(β-<2-methoxy-5-chlorobenzamido>-ethyl)-benzenesulfochloride and 2.5g of triethylamine in 100 ml benzene. Then the whole is filtered off while hot from the undissolved matter, and the crystals which are obtained while cooling the filtrate, are boiled out with methanol. After recrystallization from methanol/dimethylformamide/water, the 1-[4-(β-<2-methoxy-5-chlorobenzamido>-ethyl)-benzenesulfonyl]-3-(4.4-dimethylcyclohexyl)-parabanic acid melts at 196°–197°C.

b. 0.5 g of the above-mentioned parabanic acid is heated in a vapor bath in 5 ml of dioxane and 10 ml of 1N-sodium hydroxide solution for 45 minutes. After cooling, water is added, acidified and the N-[4-(β-<2-methoxy-5-chlorobenzamido>-ethyl)-benzenesulfonyl]-N'-(4.4-dimethylcyclohexyl)-urea obtained is recrystallized from methanol (melting point 177°–178°C).

EXAMPLE 22

N-[4-(β-<2-methoxy-5-chloro-benzamido>-ethyl)-benzenesulfonyl]-N'-(4.4-dimethyl-cyclohexyl)-urea 1. 2.9 g of N-[4-(β-<2-methoxy-5-chlorobenzamido>-ethyl)- benzene-sulfonyl]-N'-(4.4-dimethylcyclohexyl)-thiourea (prepared by reaction of 4-[β-<2-methoxy-5-chlorobenzamido>-ethyl]-benzenesulfonamide with cyclohexyl mustard oil in dioxane/acetone in the presence of potassium carbonate) melting point 175°–177°C and decomposition, are dissolved in 250 ml acetone. An aqueous solution of 0.7 g sodium nitrite is added and while stirring is continued at 5°C, 15 ml of 5N acetic acid are added dropwise. After stirring for 2½ hours acetone is distilled off. The residue is dissolved in dilute sodium hydroxide solution, the solution is clarified with charcoal and acidified. There is obtained a crystalline precipitate of N-[4-(β-<2-methoxy-5-chlorobenzamido>-ethyl)-benzenesulfonyl]-N'-(4.4-dimethylcyclohexyl)-urea, which is filtered off with suction and recrystallized from dilute methanol. The substance melts at 174°–176°C. 2. (a) 5.38 g of N-[4-(β-<2-methoxy-5-chlorobenzamido>-ethyl)benzene-sulfonyl]-N'-(4.4-dimethylcyclohexyl)-thiourea are dissolved in 5 ml dioxane and 250 ml methanol. Then 2.16 g of mercury peroxide are added and stirring is continued for 4 hours at 60°C. The mercury sulfide formed is filtered off, and the filtrate is half concentrated and water is added. After abandoning during the night a crystalline precipitate has formed, which is filtered off with suction and recrystallized from dilute methanol. The N-[4-(β-<2-methoxy-5-chlorobenzamido>-ethyl)-benzenesulfonyl]-N'-(4.4-dimethylcyclohexyl)-isoureamethylether thus obtained melts at 149°–151°C.

(b) 0.5 g of isourea ether obtained according to the method (2) (a) are dissolved in 5 ml dioxane. After addition of 20 ml 2N sodium hydroxide the whole is heated in a vapor bath for 45 minutes. By acidifying there is obtained a crystalline precipitate of N-[4-(β-<2-methoxy-5-chlorobenzamido<-ethyl)benzenesulfonyl]-N'-(4.4-dimethylcyclohexyl-urea melting at 174°–176°C after recrystallization from dilute methanol.

EXAMPLE 23

N-[4-(β-benzamido-ethyl)-benzenesulfonyl]-N'-(4.4-diethyl-cyclohexyl)-urea a. 6.4 g of 4-(β-benzamido-ethyl)-benzenesulfonamide sodium and 7.2 g of 4-(β-benzamido-ethyl)-benzenesulfonyl-carbamic acid methyl ester are well mixed. The substance is introduced into an Erlenmeyer flask having a content of 300 ml so that the bottom of the flask is covered. Then the flask is put to an oil bath pre-heated to 250°C. After a few minutes the mass starts to drip, after another 5 minutes solidification can be observed.

The whole is cooled, the reaction cake is treated with about 1 % of aqueous ammonia, it is filtered, and the filtrate is acidified with 2N hydrochloric acid. There is obtained a crystalline precipitate of N,N'-di-4-[β-(benzamido-ethyl)-benzenesulfonyl]-urea, which is dissolved once more in dilute ammonia and which precipitates by acidification with hydrochloric acid. The substance melts after filtration with suction and recrystallization at 204°C and decomposition.

b. 3.17 g of the bis-urea, obtained according to method (a) are suspended in 100 ml dioxane. 0.78 g of 4.4-diethylcyclohexyl-amine are added while stirring and salt formation can be observed. Then the whole is heated to boiling temperature for 1 hour while stirring; after a few minutes the suspension has changed into a clear solution.

The whole is concentrated in vacuo, the residue is treated with ammonia of about 1 % strength and then it is filtered. The filtrate gives by acidification a crystalline precipitate of N-[4-(β-benzamido-ethyl)-benzenesulfonyl]-N'-(4.4-diethylcyclohexyl)-urea. The substance melts after recrystallization from methanol at 199°–201°C.

EXAMPLE 24

N-[4-(γ-<2-methoxy-5-bromobenzamido>-propyl)-benzenesulfonyl]-N'-(4.4-dimethylcyclohexyl)-urea 9 g of 4-(γ<- 2-methoxy-5-bromobenzamido>-propyl)-benzenesulfonamide sodium and 16 g of N,N-diphenyl-N'-(4.4-dimethylcyclohexyl)-urea are heated for 7 hours in an oil bath to 100°C in 30 ml of dimethylformamide. Then the whole is cooled, water and alkalies are added to the reaction mixtue and the diphenylamine which has formed is etherized. The aqueous phase is treated with charcoal and the filtrate is acidified. The sulfonyl-urea obtained is recrystallized from methanol/water and melts at 192°C.

In analogous manner there is obtained:
N-[4-(γ<- 2-methoxy-5-bromobenzamido>-propyl)-benzenesulfonyl]-N'-(2.4-dimethylcyclohexyl)-urea, melting point 184°C (from methanol/water),
N-[4-(β-<2-methoxy-5-chlorobenzamido>-propyl)-benzenesulfonyl]-N'-(4.4-dimethylcyclohexyl)-urea, melting point 153°C (from methanol/water)
N-[4-(β-<2-methoxy-5-chlorobenzamido>-propyl)-benzenesulfonyl]-N'-(2.4-dimethylcyclohexyl)-urea, melting point 181°C (from methanol/water)
N-[4-(β-naphth-<1'>-amidoethyl)-benzenesulfonyl]-N'-(2.4-dimethylcyclohexyl)-urea, melting point 216°C (from methanol/water) and
N-[4-(β-tetralincarb-<2'>-amidoethyl)-benzenesulfonyl]-N'-(2.4-dimethylcyclohexyl)-urea, melting point 167°C (from methanol/water).

EXAMPLE 25

N-[4-(β-<2-methoxy-5-chlorobenzamido>-α-methylethyl)-benzenesulfonyl]-N'-(4.4-diethyl-cyclohexyl)-urea 9.6 g of 4-(β-<2-methoxy-5-chlorobenzamido>α-methylethyl)-benzenesulfonamide are dissolved in 250 ml of dioxane. 6.9 g of finely ground potassium carbonate are added and the whole is heated to boil for 2 hours while stirring. 4.5 g of 4.4-diethylcyclohexylisocyanate are added dropwise while continuing to stir. Stirring and heating is continued for 8 hours, the whole is poured into water and acidified. The crystalline precipitate obtained is filtered off with suction and dried. The whole is dissolved in dimethylformamide, methanol is added and thus a crystalline mass is obtained of N-[4-(β-<2-methoxy-5-chlorobenzamido>α-methyl)- ethyl-benzenesulfonyl]-N'-(4.4-diethyl-cyclohexyl)-urea melting at 161°–163°C.

We claim:
1. Benzenesulfonyl- ureas corresponding to the formula

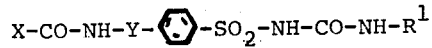

wherein R¹ is lower alkyl-cyclopentyl, X is

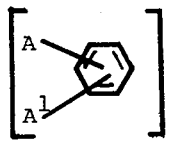

phenyl which is substituted in the 2-position by methoxy and in 5-position by halogen, methyl or methoxy, Y is a saturated hydrocarbon chain of 1-3 carbon atoms, or a salt thereof of pharmaceutically acceptable bases.

2. The compound of claim 1 wherein X is

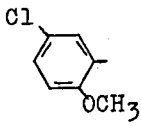

3. The compound of claim 1 wherein X is

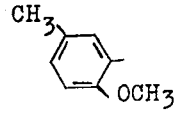

4. The compound of claim 1 wherein Y is -CH₂-CH₂-.

5. The compound of claim 1 wherein X is 2-methoxy-5-methylphenyl, Y is -CH₂-CH₂- and R¹ is 3-methylcyclopentyl.

6. The compound of claim 1 wherein X is 2-methoxy-5-chlorophenyl, Y is -CH₂CH₂- and R¹ is 3-methylcyclopentyl.

7. The compound of claim 1 wherein X is 2-methoxy-5-bromophenyl, Y is -CH₂CH₂- and R¹ is 3-methylcyclopentyl.

8. Benzenesulfonyl ureas corresponding to the formula

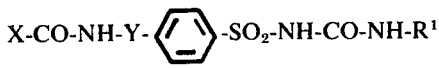

wherein R¹ is lower alkyl cyclopentyl; X is phenyl which is substituted in 2-position by lower alkoxy; Y is a saturated hydrocarbon chain of 1 to 3 carbon atoms, or a salt thereof of pharmaceutically acceptable bases.

9. The compound of claim 8 wherein X is 2-methoxyphenyl, Y is -CH₂CH₂- and R¹ is 3-methylcyclopentyl,

* * * * *

UNITED STATES PATENT AND TRADEMARK OFFICE
CERTIFICATE OF CORRECTION

PATENT NO. : 3,932,503
DATED : January 13, 1976
INVENTOR(S) : Helmut Weber, Walter Aumüller, Karl Muth and Rudi Weyer It is certified that error appears in the above-identified patent and that said Letters Patent are hereby corrected as shown below:

In the Heading between Items [63] and [52] insert:

-- [30] Foreign Application Priority Data

| Date | Country | Number |
|---|---|---|
| May 28, 1966 | Germany | F 49 329 |
| April 18, 1967 | Germany | F 52 152 |
| August 10, 1967 | Germany | F 53 202 |
| February 25, 1969 | Germany | P 19 09 272 -- |

Signed and Sealed this sixth Day of April 1976

[SEAL]

*Attest:*

RUTH C. MASON
*Attesting Officer*

C. MARSHALL DANN
*Commissioner of Patents and Trademarks*